US008876762B2

(12) United States Patent
Dayan et al.

(10) Patent No.: US 8,876,762 B2
(45) Date of Patent: Nov. 4, 2014

(54) NASOGASTRIC AND OROGASTRIC FEEDING DEVICES, SYSTEM COMPRISING THEM, METHODS AND USES THEREOF

(75) Inventors: Moshe Dayan, Rosh Ha'Ayin (IL); Ofer Pintel, Matan (IL)

(73) Assignee: Lunguard Ltd., Omer (IL)

( * ) Notice: Subject to any disclaimer, the term of this patent is extended or adjusted under 35 U.S.C. 154(b) by 750 days.

(21) Appl. No.: 13/054,977

(22) PCT Filed: Jul. 30, 2009

(86) PCT No.: PCT/IL2009/000745

§ 371 (c)(1), (2), (4) Date: Jan. 20, 2011

(87) PCT Pub. No.: WO2010/016054

PCT Pub. Date: Feb. 11, 2010

(65) Prior Publication Data

US 2011/0130650 A1 Jun. 2, 2011

Related U.S. Application Data

(60) Provisional application No. 61/085,864, filed on Aug. 3, 2008.

(51) Int. Cl.

*A61M 29/00* (2006.01)
*A61M 31/00* (2006.01)
*A61J 15/00* (2006.01)

(52) U.S. Cl.

CPC ...... *A61J 15/0003* (2013.01); *A61J 2015/0084* (2013.01); *A61J 15/0073* (2013.01); *A61J 15/0049* (2013.01); *A61J 2015/0088* (2013.01)
USPC .................. 604/101.01; 604/99.01; 604/516; 604/909

(58) Field of Classification Search

CPC . A61J 15/0003; A61J 15/0007; A61J 15/003; A61J 15/0046; A61J 15/0049; A61J 15/0073; A61J 2015/0084; A61J 2015/0088; A61J 2015/008
USPC .............. 604/503, 508, 509, 514, 516, 99.01, 604/99.02, 101.01, 101.03, 101.05, 264, 604/909, 910, 912, 915, 919, 920; 600/350
See application file for complete search history.

(56) References Cited

U.S. PATENT DOCUMENTS 4,180,076 A * 12/1979 Betancourt .............. 604/101.03
5,222,980 A * 6/1993 Gealow ........................ 623/3.12

(Continued)

FOREIGN PATENT DOCUMENTS

CN 2072842 3/1991
CN 2072842 U * 3/1991

(Continued)

OTHER PUBLICATIONS

International Preliminary Report on Patentability for parent (priority) PCT application serial No. PCT/IL2009/000745, issued Oct. 28, 2011.

(Continued)

*Primary Examiner* — Andrew Gilbert
(74) *Attorney, Agent, or Firm* — Marsteller & Associates, P.C.

(57) ABSTRACT

The present invention relates to the field of medical devices. Specifically, the invention relates to an enteral feeding device comprising expandable means which prevents or significantly reduces aspirations from the alimentary tract to the respiratory system. In further aspects, the invention relates to systems comprising said enteral feeding device, methods and uses thereof.

15 Claims, 17 Drawing Sheets

(56) References Cited

U.S. PATENT DOCUMENTS

| | | | | |
|---|---|---|---|---|
| 5,456,251 | A | 10/1995 | Fiddian-Green | |
| 5,560,747 | A * | 10/1996 | McCue et al. | 606/196 |
| 5,765,559 | A * | 6/1998 | Kim | 128/207.15 |
| 6,468,200 | B1 * | 10/2002 | Fischi | 600/18 |
| 6,488,653 | B1 * | 12/2002 | Lombardo | 604/103.06 |
| 6,773,452 | B2 * | 8/2004 | Shaker | 600/587 |
| 8,303,567 | B2 * | 11/2012 | Stedman et al. | 604/511 |
| 2005/0096636 | A1 * | 5/2005 | Freyman et al. | 604/537 |
| 2005/0215948 | A1 | 9/2005 | Adams | |
| 2006/0020278 | A1 * | 1/2006 | Burnett et al. | 606/153 |
| 2006/0276746 | A1 | 12/2006 | Burnside et al. | |
| 2007/0080223 | A1 | 4/2007 | Japuntich | |
| 2007/0270892 | A1 | 11/2007 | Makower et al. | |
| 2007/0282219 | A1 | 12/2007 | Holte | |
| 2008/0071202 | A1 | 3/2008 | Nardi et al. | |
| 2008/0077043 | A1 * | 3/2008 | Malbrain et al. | 600/547 |
| 2008/0086076 | A1 * | 4/2008 | Gerber | 604/43 |
| 2008/0154191 | A1 * | 6/2008 | Gobel | 604/101.05 |
| 2008/0171963 | A1 | 7/2008 | Gerber | |
| 2008/0249461 | A1 * | 10/2008 | Foreman et al. | 604/28 |
| 2008/0319504 | A1 * | 12/2008 | Loushin et al. | 607/40 |

FOREIGN PATENT DOCUMENTS

| | | | |
|---|---|---|---|
| CN | 2336816 | Y * | 9/1998 |
| CN | 2336816 | Y | 9/1999 |
| EP | 1892010 | A1 | 2/2008 |
| JP | 2008049160 | A | 3/2008 |
| JP | 2008509730 | A | 4/2008 |
| WO | 01/24860 | | 4/2001 |
| WO | 01/72221 | A1 | 10/2001 |
| WO | 2006020441 | A2 | 2/2006 |
| WO | 2008/121603 | A1 | 10/2008 |
| WO | 2009/027864 | | 3/2009 |

OTHER PUBLICATIONS

International Preliminary Report on Patentability (IRPR) for parent PCT application serial No. PCT/IL2009/000745, issued Feb. 8, 2011.

Patent Office for Australia, Office Action, issued Aug. 22, 2013, for counterpart patent application serial No. 2009278778.

Patent Office for the People Republic of China. Office Action, issued Sep. 29, 2013, for counterpart patent application serial No. 20090130448.2 (with translation).

Patent Office for the European Patent Office, Extended European Search Report, issued Feb. 7, 2014, for counterpart patent application serial No. 09804643.6.

Patent Office for Japan, Office Action, mailed Mar. 4, 2014, for counterpart patent application serial No. 2011-521683 (with translation).

* cited by examiner

NASOGASTRIC AND OROGASTRIC FEEDING DEVICES, SYSTEM COMPRISING THEM, METHODS AND USES THEREOF

FIELD OF THE INVENTION

The present invention relates to the field of medical devices. Specifically, the invention relates to an enteral feeding device, which is an orogastric or nasogastric feeding device, comprising expandable means which prevents or significantly reduces aspirations from the alimentary tract to the respiratory system. In further aspects, the invention relates to systems comprising a feeding tube with expandable means, methods and uses thereof.

BACKGROUND OF THE INVENTION

Hospitalized ventilated patients and patients that require emergent intubation (crush induction) are at increase risk for reflux of gastroesophageal contents. These populations are at risk for longer Length of Staying (LOS) or dying, not only from their critical illness but also from secondary processes such as nosocomial infection. Pneumonia is the second most common nosocomial infection in critically ill patients, affecting 27% of all critically ill patients [1], and is responsible for almost half of the infections in critically ill patients in Europe [2]. Eighty-six percent of nosocomial pneumonias are associated with mechanical ventilation and are termed ventilator-associated pneumonia (VAP). Between 250,000 and 300,000 cases per year occur in the United States alone, which is an incidence rate of 5 to 10 cases per 1,000 hospital admissions [3]. An independent contribution to mortality conferred by ventilator-associated pneumonia was recently suggested [4]. The mortality attributable to VAP has been reported to be as high as 50% [5]. Ventilator-associated pneumonia causes substantial morbidity by increasing the duration of mechanical ventilation and intensive care unit stay [6].

Beyond mortality, the economics of VAP include increased intensive care unit (ICU) LOS from 4 to 13 days, and incremental costs associated with VAP have been estimated at between $5,000 and $20,000 per diagnosis [7].

A growing body of evidence suggests that, in the presence of a functional gut, nutrition should be administered through the enteral route largely because of the morbidity associated with other modes of feeding. Furthermore, enteral alimentation is currently the most widely used modality for providing nutrition support in the ICU [8]. Favorable effects of enteral feeding include better substrate utilization, prevention of mucosal atrophy, and preservation of gut flora, integrity, and immune competence [9]. Therefore, there has been an increased interest among physicians to feed patients through the enteral route as soon as possible. Previous studies looking at critically ill patients with abdominal surgery, hip fracture, burn, and trauma demonstrated beneficial effects of early enteral feeding [10]. However, a report from critically ill medical patients suggested that early feeding to satisfy the patient's nutritive needs resulted in more harm and was associated with greater infectious complications [11].

In the pathogenesis of VAP, bacterial colonization of the oral cavity and subsequent aspiration of oropharyngeal fluids along the endotracheal tube are pivotal and should be prevented [12]. However, infectious hazards, tissue injury, and aspiration associated with placement and maintenance of orogastric and nasogastric tubes used for the delivery of enteral nutrition suggest that not all patients benefit of adequate preventive procedures. Bacterial colonization of the stomach and gastroesophageal aspiration is mainstay in the pathogenesis of VAP [13]. Gastroesophageal aspiration is facilitated by the presence of a nasogastric tube and a supine body position [14]. Experimental studies with radioactive-labeled enteral feeding indeed suggested that endotracheal aspiration of gastric contents occurred more frequently when patients were placed in supine rather than semi recumbent position [15]. On the basis of these findings, the Centers for Disease Control and Prevention advised treatment of mechanically ventilated patients in a semi recumbent position as a VAP-preventive measure [16].

Clinicians can focus on eliminating or minimizing the incidence of VAP through preventive techniques. While little has affected the incidence of late-onset VAP, the occurrence of early-onset VAP can be reduced by simple measures such as placing a patient, in a semi recumbent position. Yet, even apparently simple preventive measures are not easy to control: it was shown that health care team compliance rates is insufficient and varies between 30% and 64% [17]. The medical challenge of preventing contamination of the respiratory pathways by gastrointestinal reflux in ventilated patients is well known in the Art. Several technical solutions were proposed as it can be appreciated in the following brief review.

US 2008/0171963 relates to a device that prevent aspiration of gastric fluids in patients being fed or medicated through a gastric tube and placed in a semi-recumbent position. The device comprises an angle sensor fixed to said patient and an electrical control circuit which may stop the flow in the gastric tube if the patient is reclining beyond a predetermined angle, thereby decreasing the risks of aspiration. However, US 2008/0171963 is unsuitable in all the cases were the patient should be placed in supine position and not in semi-recumbent position.

WO 01/24860 relates to an artificial airway device comprising a laryngo-pharyngal mask including a roughly elliptical expandable masking ring. The expandable mask sealingly surrounding the laryngeal inlet when expanded to obstruct communication between the laryngeal inlet and esophagus to avoid reflux of gastric contents. A gastro-tube provides a fluid flow-path to the surface of the mask facing the esophagus when the mask sealingly surrounds the laryngeal inlet. However, this inflatable laryngo-pharyngal mask is blocking the natural flow of saliva from the oral cavity to the stomach. Moreover, laryngo-pharyngal masks cannot be applied for long periods of time as the pressure exerted on the esophagus sidewalls by the expandable element may cause irreversible damages on epithelial tissues.

WO 2009/027864 relates to an enteral feeding unit that helps to reduce the occurrence of gastro-esophageal-pharyngeal reflux during enteral feeding. The unit, comprises a gastric sensor placed within the stomach and a sealing element placed within the esophagus. When the gastric sensor reports a pressure increase into the stomach, the esophagus is sealed to avoid the reflux of gastric contents. However, complete sealing of the esophagus pathway may be problematic as it avoids deglutition of saliva, and reflux of accumulated saliva may be wrongly redirected into the airway system. Furthermore, long time appliance of high pressure on the esophagus sidewalls may cause severe damages to the epithelial tissues.

Therefore, there is a need for a device that is deployable by any trained caregiver personnel for the prevention or reduction of aspirations from the alimentary tract to the respiratory system.

It is therefore an object of the invention to provide a device which enables feeding a patient in need through an enteral route and which also prevents, or significantly reduces, gastro-esophageal reflux from the alimentary tract to the respiratory system.

It is another object of the invention to provide a device which enables feeding a patient in need through an enteral route and allow the swallowing of saliva, nasopharynx and oropharynx secretions.

It is a further object of the invention to provide a device which enables feeding a patient in need through an enteral route without damaging epithelial esophagus tissues.

It is a further object of the invention to provide a system which enables feeding a patient in need through an enteral route, and which can control and monitor the transit of fluids and biological secretions in the esophagus.

It is a further object of the invention to provide a method for significantly reducing vomiting events in an enterally fed patient.

It is a further object of the invention to provide a method for the insertion and the correct positioning of a feeding tube into the esophagus of a patient in need of enteral feeding.

Further purposes and advantages of this invention will appear as the description proceeds.

SUMMARY OF THE INVENTION

In a first aspect, the present invention relates to an enteral feeding device comprised of an elongated flexible hollow element, the element comprising:

a) a distal section comprising at least one feeding aperture;

b) a middle section comprising at least three expandable means localized around the elongated flexible hollow element; and c) a proximal section comprising a food connector, at least one fluid connector for each of the expandable means, and optionally, a positioning marker;

wherein each of the fluid connectors is in fluid connection with one of the expandable means via an individual fluid conveying channel, and wherein the food connector is in fluid connection with the feeding aperture(s) via a food conveying channel.

The elongated flexible hollow element of the enteral feeding device is made of either a single piece of a biocompatible flexible material such as silicone, latex, PVC and polyurethane, or of several rigid or semi-rigid interconnected biocompatible elements. Radiopaque markers may be embedded into the wall of the elongated flexible hollow element. The expandable means, when inflated, have either a round or a cylindrical shape, and are distant from 0 to 10 mm one to each other, preferably about 0 mm. The distal section of the feeding device may comprise at least one expandable means, and the proximal section may comprise a positioning marker. Moreover, the feeding device of the invention may comprise at least one element selected from the group consisting of a sensing element, a stimulating element, a suction element, a sprinkling element.

In a second aspect, the present invention relates to an enteral feeding device comprised of an elongated flexible hollow element, the element comprising:

a) a distal section comprising at least one feeding aperture, and an expandable means;

b) a middle section; and c) a proximal section comprising a food connector, an inflation mechanism, at least one relief valve, and at least one pressure sensor;

wherein the inflation mechanism, the relief valve(s), and the pressure sensor(s) are all in fluid connection with the expandable means via a fluid conveying channel, and wherein the food connector is in fluid connection with the feeding aperture(s) via a food conveying channel.

In a third aspect, the present invention relates to a system for controlling fluids motion into the esophagus of a subject, the system comprising:

a) an enteral feeding device as described in the first aspect of the invention;

b) a control and monitoring unit;

c) a feeding unit comprising a feeding pump; and d) a processing unit comprising a processor, a memory, an input, device, a display, and dedicated software, wherein the processing unit is provided either as a single element or as several separated elements.

The control and monitoring unit typically comprises a first fluidic system adapted to provide a pressurized fluid, a second fluidic system adapted to provide a vacuum, a set of electrical and/or pneumatic valves, and a set of pressure sensors. Additionally, the control and monitoring may comprise one or more components selected from the group consisting of a sensor, a biosensor, a suction system, and a sprinkling system.

In a fourth aspect, the present invention relates to a method for reducing aspirations from the alimentary tract in an enterally fed patient, the method comprising the steps of:

a) providing a system as described in the third aspect of the invention;

b) positioning the enteral feeding device provided in the system in the esophagus of a patient;

c) feeding the patient with a nutritive solution; and d) simulating peristaltic waves with the expandable means of the feeding device, thereby pushing gastrointestinal fluids back to the stomach and allowing the passage of oropharynx fluids.

In this method, the peristaltic waves simulated by the system may be synchronized with the natural peristaltic movements of the esophagus.

In a fifth aspect, the present invention relates to a method for reducing the amount of gastrointestinal fluids that reaches the oropharynx of an enterally fed patient during vomiting events, the method comprising the steps of:

a) providing a system as described in the third aspect of the invention;

b) positioning the enteral feeding device provided in the system in the esophagus of a patient;

c) feeding the patient with a nutritive solution;

d) determining if an amount of gastrointestinal fluids is rising up into the esophagus; and e) optionally, inflating all the expandable means of the enteral feeding device, thereby sealing the esophagus of the patient and redirecting gastrointestinal fluids towards the stomach.

In a sixth aspect, the present invention relates to a method for positioning, in the esophagus of a patient, an enteral feeding device of the first aspect comprising a positioning marker in its proximal section, the method comprising the steps of:

a) providing means for measuring the fluid pressure inside each of the expandable means individually (e.g. the control and monitoring unit as described above);

b) determining that all the expandable means of the feeding device are deflated;

c) inserting the device in the esophagus of a patient via either the nasal or oral route until the positioning marker reaches the mouth or nose of the patient;

d) inflating one of the expandable means;

e) pulling back slowly the feeding device, until the pressure measuring means indicates that the pressure inside the inflated expandable means has risen above a predetermined threshold; and f) deflating the inflated expandable means; and g) optionally, further pulling back slowly the feeding device by a predetermined distance.

In a seventh aspect, the present invention relates to a method for positioning, in the esophagus of a patient, an enteral feeding device of the first aspect comprising radiopaque markers, the method comprising the steps of:

a) determining that all the expandable means of the device are deflated;

b) providing a X-ray imaging system;

c) inserting the device in the esophagus of a patient via either the nasal or oral route;

d) using the X-ray imaging system to monitor the position of the radiopaque markers in the esophagus of the patient;

e) moving the device in the esophagus of the patient until the radiopaque markers indicates that, the proximal expandable means of the middle section is placed about 5 cm beneath the carina.

In the eighth aspect, the present invention relates to a method for positioning a feeding device as described in the second aspect, in the esophagus of a patient, the method comprising the steps of:

a) determining that the expandable means of the device is deflated;

b) inserting the device in the esophagus of a patient via either the nasal or oral route;

c) inflating the expandable means by actuating the inflation mechanism;

d) pulling back slowly the feeding device until the pressure sensor indicates that the pressure inside the expandable means has risen above a predetermined threshold; and e) deflating the expandable means via the relief valve.

All the above and other characteristics and advantages of the invention will be further understood through the following illustrative and non-limitative description of preferred embodiments thereof, with reference to the appended drawings. In the drawings the same numerals are sometimes used to indicate the same elements in different drawings.

BRIEF DESCRIPTION OF THE DRAWINGS

The above and other characteristics and advantages of the invention will be more readily apparent through the following examples, and with reference to the appended drawings, wherein.

DETAILED DESCRIPTION OF PREFERRED EMBODIMENTS

The first aspect of the present invention relates to an enteral feeding device that enables the administration of nutritive solutions directly into the stomach of a patient, significantly reduces the risks of aspirations from the alimentary tract into the respiratory system (estimated by the Inventors as being at least 50% reduction of the cases), and allows deglutition of biological fluids secreted in the upper part of the digestive system into the stomach (for instance saliva, nasopharynx secretions, and oropharynx secretions). The device of the present invention is preferably disposable.

Figure 1:
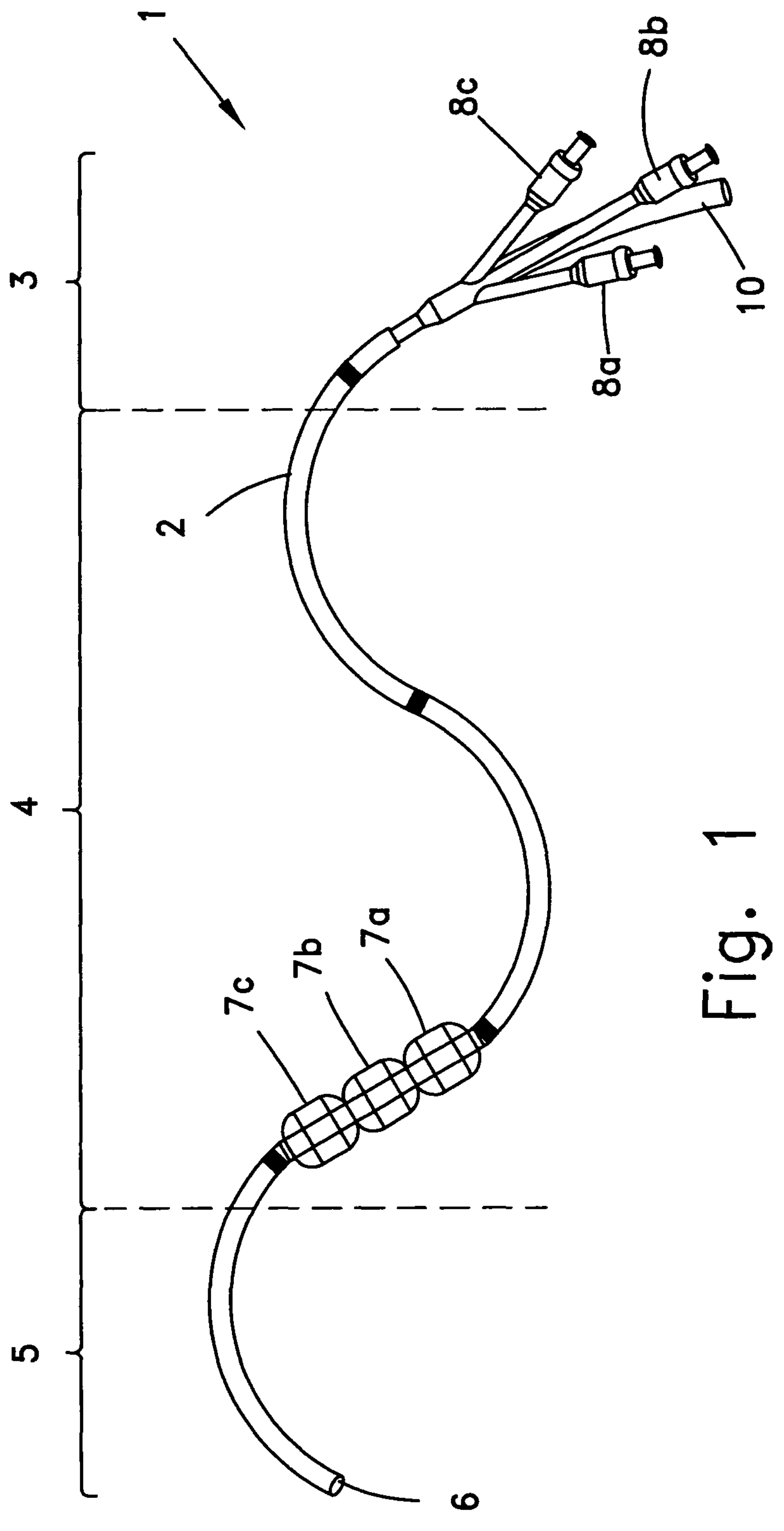
FIG. 1 is a schematic view of an embodiment of the device of the invention.

With reference to FIG. 1, the feeding device 1 of the invention comprises an elongated flexible hollow element 2, a proximal section 3, a middle section 4, and a distal section 5. Typically, the elongated flexible element 2 is made of a single piece of a biocompatible flexible material, or several rigid or semi-rigid interconnected biocompatible parts, which allow the flexible element 2 to be bent in such a way that it can be safely introduced into the esophagus of a patient. In a specific embodiment of the device of the invention, the element 2 is made of a flexible biocompatible polymer material such as silicone, latex, PVC or polyurethane. The element 2 may be optionally coated with one or more protective layers that avoid colonization of microorganisms or degradation by biological fluids. The diameter of element 2 is typically of between 2 mm and 10 mm and its length is from about 30 mm (preterm newborn) to about 150 mm (adults).

The distal section 5 of the feeding device 1 comprises one or more feeding apertures 6, which are located either in a central position at the end of element 2 or laterally near the end of element 2. These apertures 6 enable the delivery of a nutritive solution through a hollow conduit of element 2 into the stomach. Optionally, at least one expendable element may be placed around the distal end of tube 2 to ease the positioning of the device 1 into the esophagus of the patient or serve as a pressure sensor, as it will be explained later.

The middle section 4 of the feeding device 1 comprises at least three expandable means 7*a*, 7*b* and 7*c* surrounding the flexible element 2, which can be inflated or deflated by introducing or draining a fluid into their interior. The fluid used should be safe for the patient and preferably in a gas or liquid form, e.g. air or water (herein the word fluid is used to designate any medically acceptable gas or liquid used in the art to inflate expandable means). The expandable means 7*a*, 7*b* and 7*c* are typically made of a flexible biocompatible membrane having a thickness of between 0.1 mm and 1 mm, which is attached to the side wall of element 2. When deflated, the expandable means 7*a*, 7*b* and 7*c* lay against the side wall of the flexible element 2, enlarging the diameter of element 2 by less than 1 mm. When inflated, the expandable means 7*a*, 7*b* and 7*c* reach a diameter up to about 20 mm, thereby enabling the sealing of the esophagus lumen. According to the specific embodiment of the device of the invention, the expandable means 7*a*, 7*b* and 7*c* may be placed at diverse position on the middle section 4, but two contiguous expandable means are separated by no more than 10 mm, preferably 0 mm. When inflated, the expandable means 7*a*, 7*b* and 7*c* may have several shapes, but have preferably a round shape or a cylindrical shape. In the later case, the length of the sides of said cylinder is typically between about 10 mm and 30 mm, the side facing the epithelium of the esophagus.

The proximal section 3 of the feeding device 1 is terminated by at least three fluid connectors 8*a*, 8*b* and 8*c*, each one being prolonged, within the flexible element 2, by three distinct fluid conveying channels 9*a*, 9*b* and 9*c* (see FIGS. 2A-2D) which are adapted to convoy a fluid into or from the expandable means 7*a*, 7*b* and 7*c*. Additionally, the proximal section 4 comprises at least one food connector 10, which is prolonged, within the flexible element 2, by a food conveying channel 11 (see FIGS. 2A-2D) which is adapted to convoy a nutritive solution to the stomach 37 of the patient through the apertures 6 situated in the distal section 5.

Figures 2A, 2B, 2C, 2D:
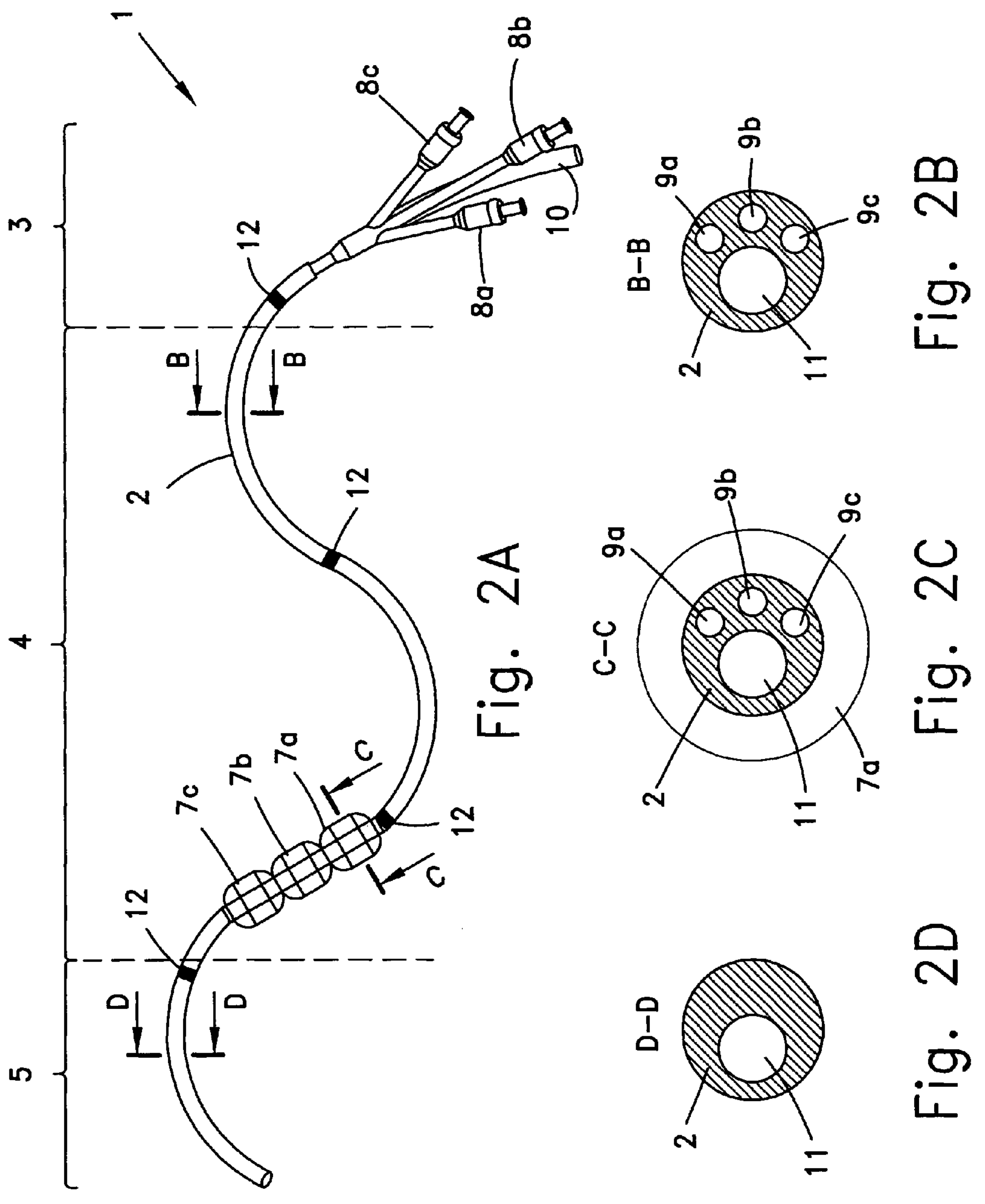
FIGS. 2A, 2B, 2C, and 2D, respectively show a perspective view and three cross-section views of an embodiment of the device of the invention.

Referring now to FIG. 2A, shown is a schematic view of one specific embodiment of the device 1 of the invention comprising an elongated flexible hollow element 2, three expandable means 7*a*, 7*b* and 7*c*, three fluid connectors 8*a*, 8*b* and 8*c*, a food connector 10 and several radiopaque peripheral markers 12. Radiopaque markers 12 are embedded within the walls of element 2, preferably in the proximal section 3 and distal section 5 to ensure a correct positioning of the device 1 inside the patient's esophagus under X-ray monitoring.

FIG. 2B is a cross section view of the proximal section 3 of the feeding device 1, taken along line B-B shown in FIG. 2A, wherein three fluid conveying channels 9*a*, 9*b* and 9*c* and a food conveying channel 11 can be seen inside element 2.

FIG. 2C is a cross section view of the middle section 4 of the feeding device 1, taken along line C-C shown in FIG. 2A, wherein three fluid conveying channels 9*a*, 9*b* and 9*c*, and a food conveying channel 11 can be seen inside element 2, and the expandable means 7*a* can be seen surrounding element 2.

FIG. 2D is a cross section view of the distal section 5 of the feeding device 1, taken along line D-D shown in FIG. 2A, wherein the food conveying channel 11 can be seen inside element 2.

Figures 3A, 3B, 3C, 3D, 3E:
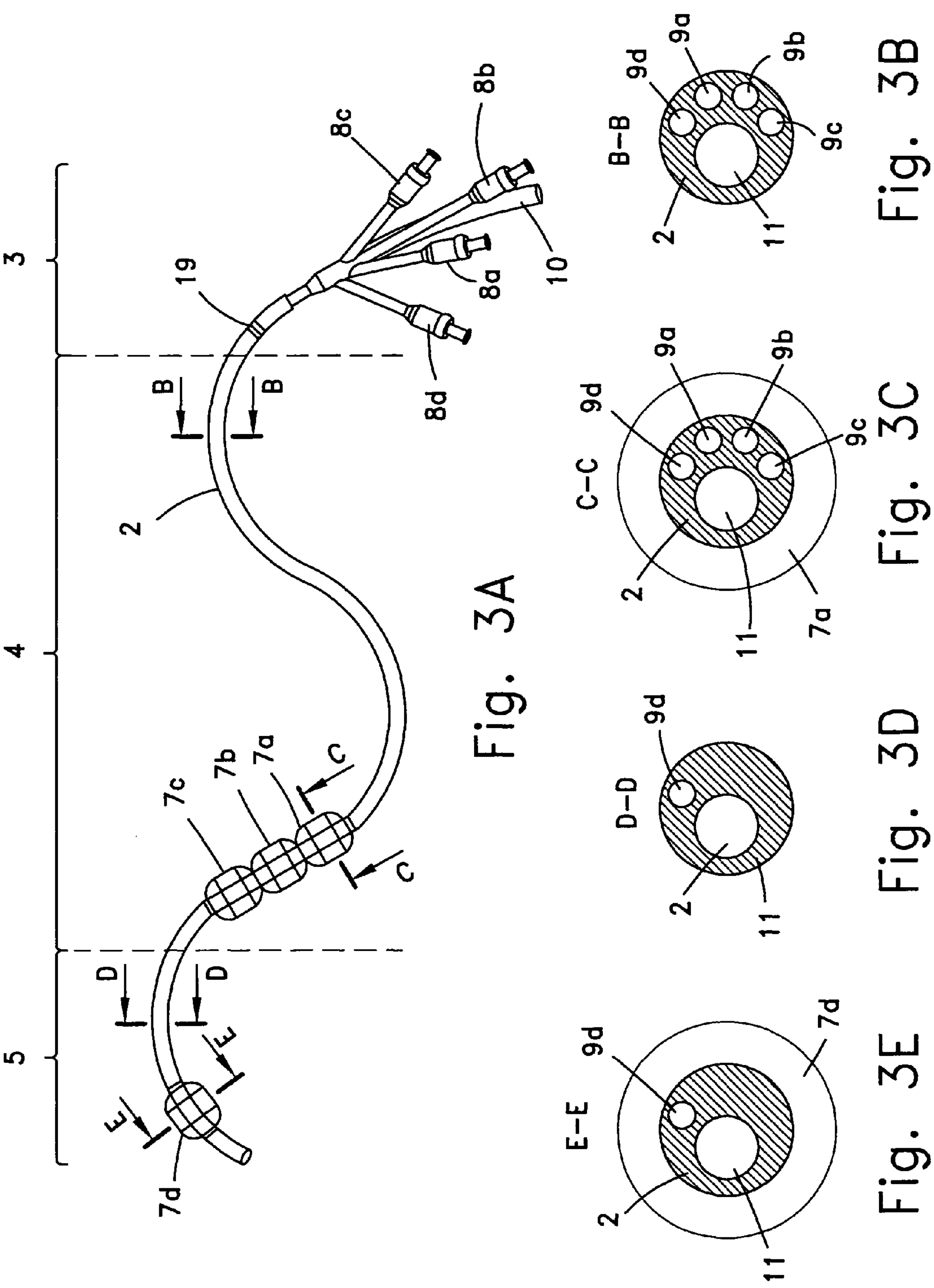
FIGS. 3A, 3B, 3C, 3D, and 3E respectively show a perspective view and four cross-section views of another embodiment of the device of the invention.

Referring to FIG. 3A, shown is a schematic view of another embodiment of the device 1 of the invention comprising an elongated flexible hollow element 2, four expandable means 7*a*, 7*b*, 7*c*, and 7*d*, four fluid connectors 8*a*, 8*b*, 8*c*, and 8*d*, and a food connector 10. Radiopaque markers are not necessary in this specific embodiment, and the correct positioning of the feeding tube is allowed by the presence of an expandable means 7*d* located on the distal section 5 of the device and a positioning marker 19 located on the proximal section 3 of said device.

FIG. 3B is a cross section view of the proximal section 3 of the feeding device 1, taken along line B-B shown in FIG. 3A, wherein four fluid conveying channels 9*a*, 9*b*, 9*c* and 9*d* and a food conveying channel 11 can be seen inside element 2.

FIG. 3C is a cross section view of the middle section 4 of the feeding device 1, taken along line C-C shown in FIG. 3A, wherein four fluid conveying channels 9*a*, 9*b*, 9*c* and 9*d*, and a food conveying channel 11 can be seen inside element 2, and the expandable means 7*a* can be seen surrounding element 2.

FIG. 3D is a cross section view of the distal section 5 of the feeding device 1, taken along line D-D shown in FIG. 3A, wherein the fluid conveying channel 9*d* and the food conveying channel 11 can be seen inside element 2.

FIG. 3E is a another cross section view of the distal section 5 of the feeding device 1, taken along line E-E shown in FIG. 3A, wherein the fluid conveying channel 9*d* and the food conveying channel 11 can be seen inside element 2, and the expandable means 7*d* can be seen surrounding element 2.

Figure 4:
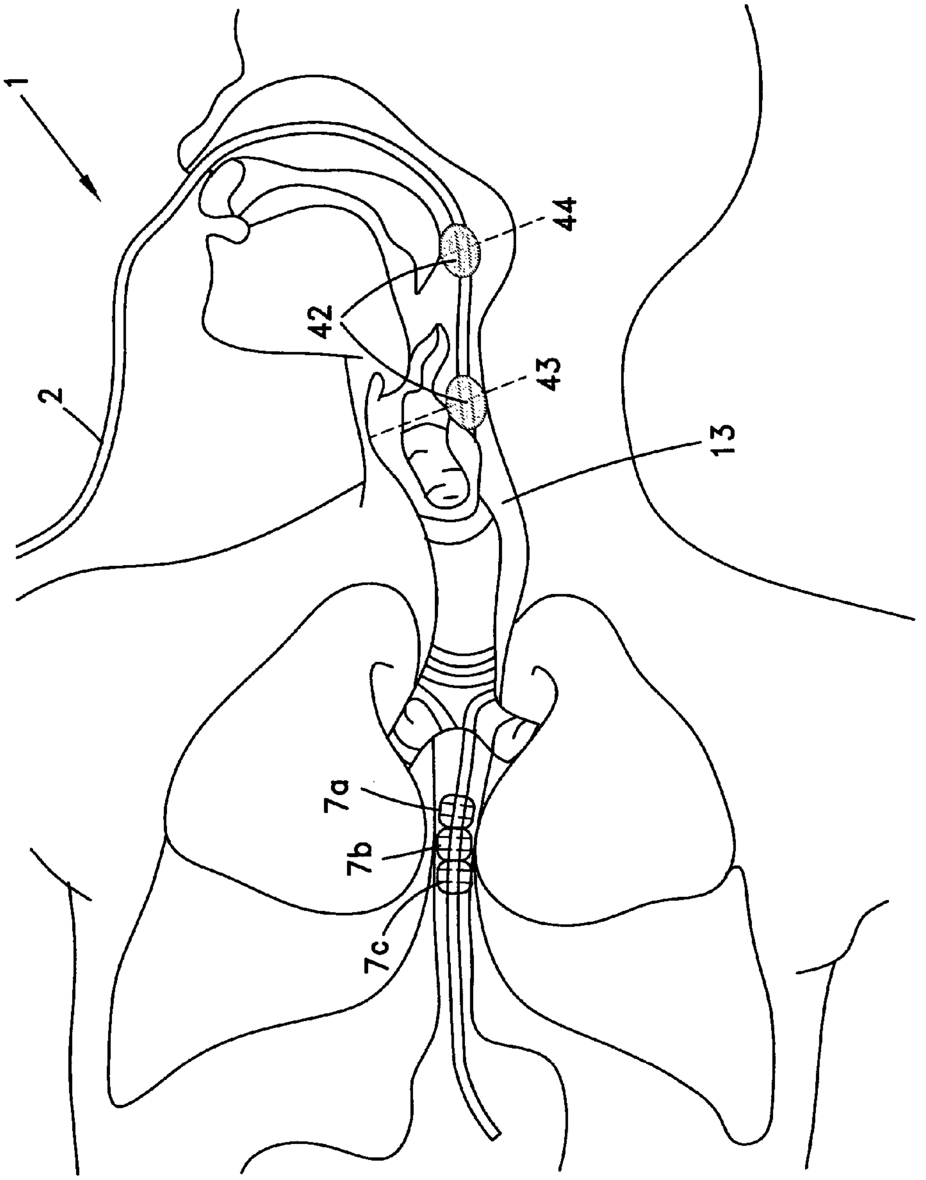
FIG. 4, is a schematic view showing an embodiment of the device of the invention comprising three expandable means and two optional places for stimulating elements.

Some embodiments of the device of the invention are totally free of any electrical elements but other embodiments of the device of the invention may comprise sensing and/or stimulating elements based on a mechanical, optical, electrical, chemical or biological signal, or any combination thereof. Sensing elements are preferably placed in internal channels, on expandable means, inside expandable means, or on the side wall of the flexible element. The sensing elements may be used to measure internal parameters such as the intra-esophagus pressure, intra-esophagus and/or stomach pH, etc. Stimulating elements are preferably placed on expandable means or on the side wall of the flexible element. The stimulating elements may be used, for instance, to stimulate an esophageal peristaltic wave, by employing either an electrical, chemical or mechanical stimulating signal. Stimulating elements 42 may be placed, for example, before the expandable means 7*a*. After insertion of device 1 in the patient's esophagus 13, a stimulating element 42 may be localized at the upper esophagus level 43, or next to the larynx/uvula 44, or at both places if required (see FIG. 4).

Ideally, the sensing elements and the stimulating elements are interconnected in order to coordinate the stimulation with the data gathered by the sensing elements. Furthermore, receiving and/or emitting elements can be included in the device of the invention, in order to communicate with the surrounding environment without the addition of electrical wires.

The feeding device of the invention not only enables the administration of a nutritive solution directly into the stomach of a patient but is also able to control the movement of fluids in the lumen of the esophagus thanks to expandable means, which can be independently inflated or deflated. The expandable means, when inflated, are used to interrupt the flow of fluid in the esophagus; when deflated, they allow the free flowing of the fluid in the esophagus; when expanding (i.e. from a deflated to an inflated condition) they exert a pressure on the fluids located in the space between the esophageal epithelium and the expanding membrane, thereby pushing the fluid out of said space. When synchronized, the sequential inflation/deflation of the expandable means can simulate a peristaltic wave, thereby forcing the fluids contained in the esophagus to move in a determined direction.

Figure 5:
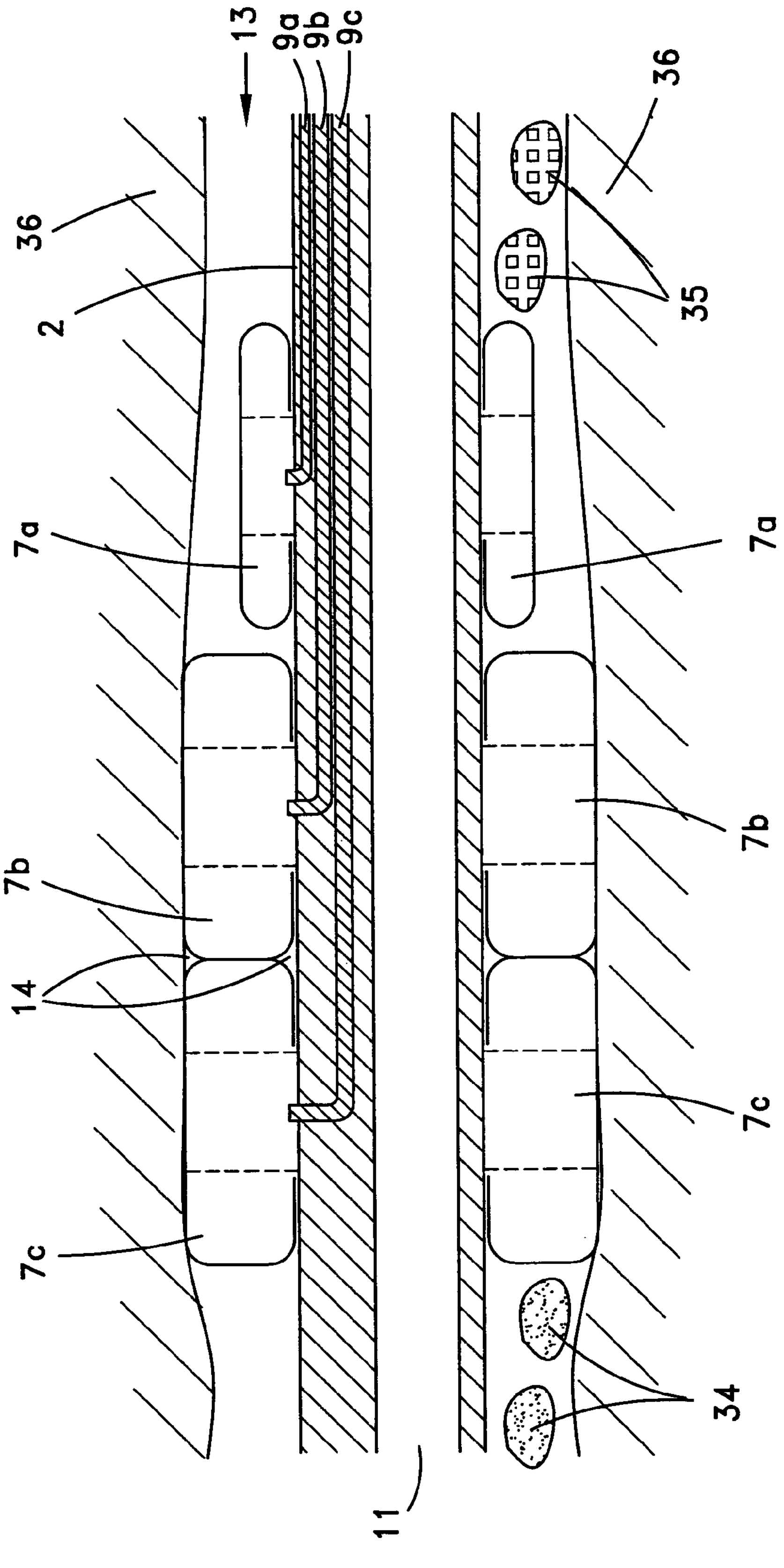
FIG. 5 is an enlarged, longitudinal, cross sectional view of a part of the middle section of an embodiment of the device of the invention, comprising expandable elements.

FIG. 5 shows an enlarged, longitudinal cross sectional view of the middle section 4 of the device 1, located in the esophagus 13 of a patient, and comprising three expandable means 7*a*, 7*b* and 7*c*. The expandable means 7*a*, 7*b* and 7*c* have been inflated by injecting a fluid in the space formed between the outer wall of the element 2 and the internal side of the expandable membrane. The fluid is injected separately in each of expandable means 7*a*, 7*b* and 7*c* through the corresponding fluid conveying channels 9*a*, 9*b* and 9*c*. When inflated, the expandable means 7*a*, 7*b* and 7*c* have a cylindrical shape or round shape and exert a low pressure (in the range of 10 mmHg to 50 mmHg) on the esophageal epithelium 36, thereby sealing the esophagus 13 and interrupting the flow of gastrointestinal fluids 34 and oropharynx fluids 35. The dead volumes 14, located between two inflated expandable means should be as small as possible (typically between about 0 $mm^3$ and 10 $mm^3$) since they may trap fluids and thereby irritating the surrounding tissue. To clean the dead volumes 14 from the trapped fluids, the device of the invention may further include sprinklers or suction elements, located between the expandable elements.

A further aspect of the invention relates to a system suitable to provide a patient with a nutritive solution, to avoid or considerably reduce occurrences of gastrointestinal reflux, and to enable fluids and secretions transiting through the oropharynx to be swallowed.

Figure 6:
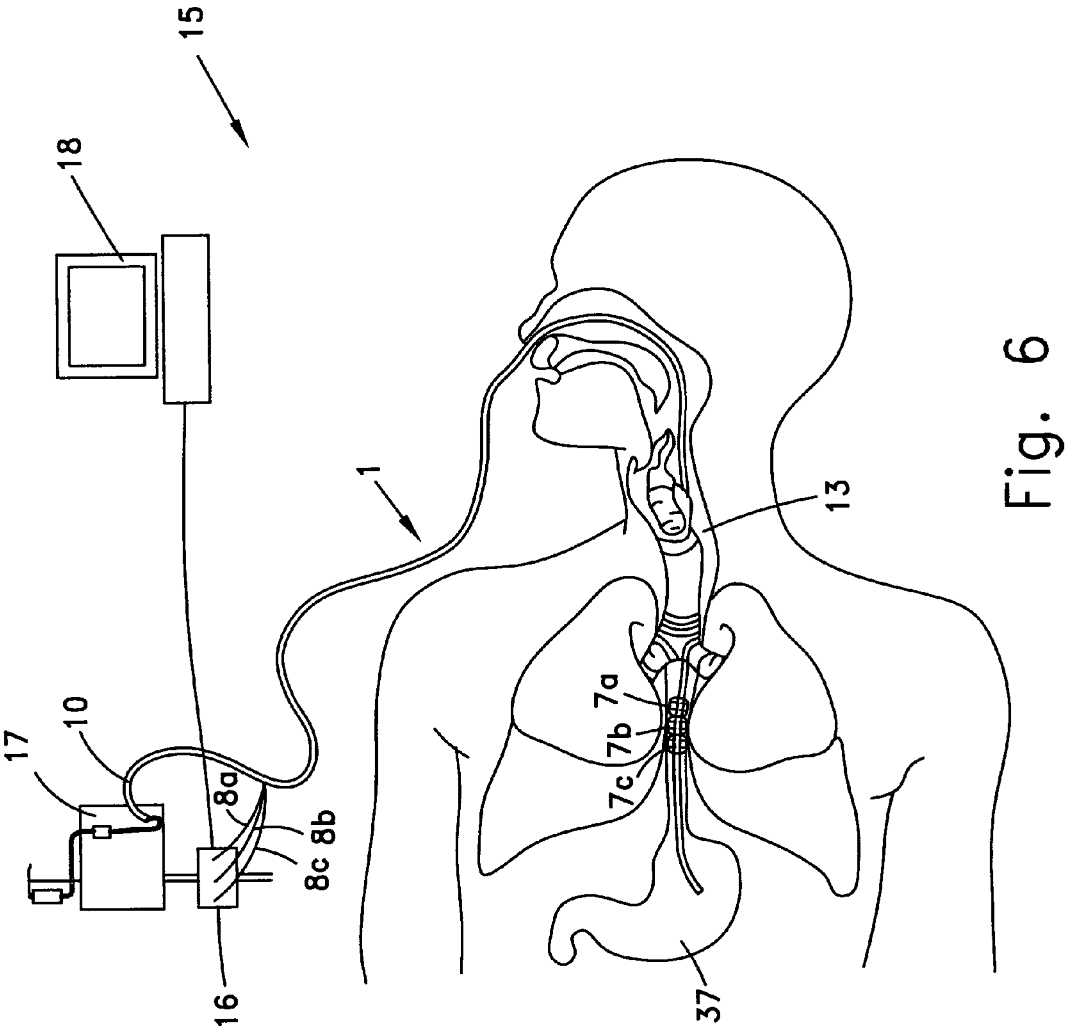
FIG. 6 is a schematic view of an embodiment of the system of the invention, which allows control and monitoring of the fluids transit into the esophageal lumen of a patient.

Referring to FIG. 6, shown is a schematic view of one embodiment of the system 15 of the invention. This embodiment allows controlling and monitoring of the transit of fluids into the esophagus 13 of a patient. The system 15 can work in a "stand-alone", mode which do not require the intervention of the medical staff, or in an "interactive" mode, wherein each action of the system 15 may be controlled by the medical staff.

The system 15 comprises a feeding device 1 (as described above) which is introduced via either nasal or oral routes into the esophagus 13. The end of the distal section 5 of device 1 is positioned into the stomach 37 of the patient, and the expandable means 7*a*, 7*b* and 7*c*, of the middle section 4, are preferably placed 5 cm beneath the carina. Methods for precise positioning of device 1 into the esophagus of a patient will be described more specifically herein below. The fluid connectors 8*a*, 8*b* and 8*c* of the feeding device 1 are plugged into a control and monitoring unit 16, and the food connector 10 is plugged into a feeding unit 17. The system shown in FIG. 6 also includes a processing unit 18 comprising a processor, a memory, an input device and a display, said unit 18 being connected to the control and monitoring unit 16. The processing unit 18 may be either provided as a single stand alone element (e.g. laptop, palm pilot with a touch screen) or as several separated elements (e.g. PC). Optionally, the processing unit 18 may be connected simultaneously to other medical systems used to diagnose and/or monitor the patient's medical status. Typically, the feeding unit 17 comprises a feeding pump which control the amount of a nutritive solution delivered to the patient through the feeding device 1.

The control and monitoring unit 16 is able to control and monitor the fluid pressure inside the body of each of the expandable means 7*a*, 7*b* and 7*c* individually. Moreover, when the expandable means are inflated, the control and monitoring unit 16 is able to sense any external pressure applied on the outer surface of an expandable means. When such external pressure is applied, a significant increase of the internal pressure of the expandable means is observed. Therefore, the peristaltic movement of the esophagus 13 may be assessed by the control and monitoring unit 16 thanks to the variations of pressure exerted on inflated expandable means, which are in direct contact with the esophageal epithelium.

The processing unit 18 collects, stores and processes in real-time the data coming from the control and monitoring unit 16. Software is included in the processing unit 18, and is used to analyze and show the critical information to the medical staff caring for the patient, onto the display. The system 15 may include an automatic or manual turn-off element that enables simultaneous deflation of all the expandable means 7, and which can be used in cases of emergency (such as uncontrolled increase of the pressure in one or more of the expandable elements).

Figure 7:
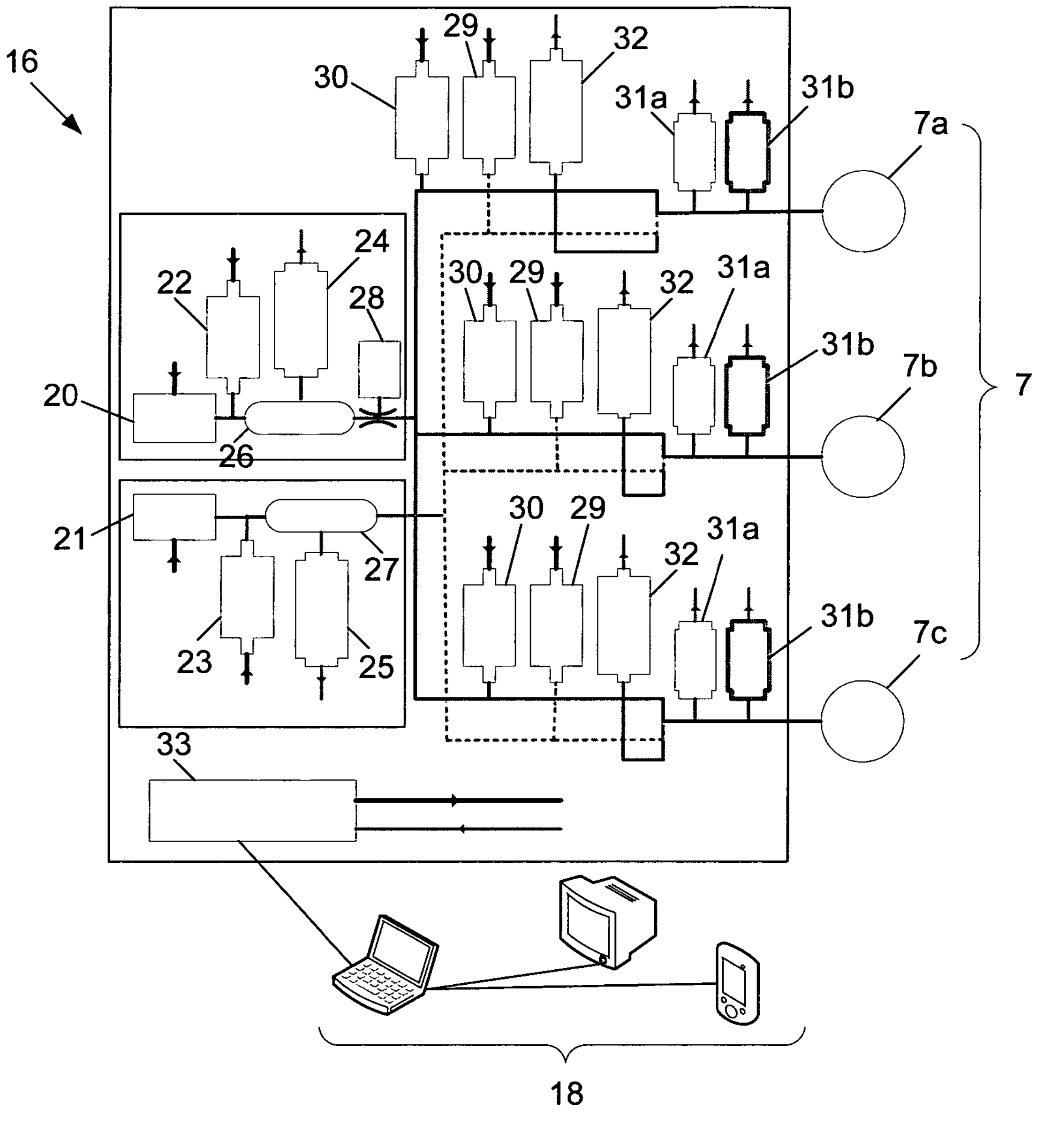
FIG. 7 is a schematic view of an embodiment of the control and monitoring unit of the system of the invention.

Referring to FIG. 7, shown is a schematic view of an embodiment of the control and monitoring unit 16 of the system of the invention. The control and monitoring unit 16 shown in FIG. 7 comprises two parallel fluidic systems and a set of electrical or pneumatic valves, in order to control the inflation and deflation of the expandable means 7. The first fluidic system provides a highly compressed fluid which can be injected inside the body of an expandable means to inflate it, whereas the second fluidic system generates a vacuum which can be used to drain the fluid from said body, thereby deflating the expandable means. In practice, the fluid pressure applied in the body of an expandable means results from the balanced action of both fluidic systems.

The first fluidic system, shown in black lines on FIG. 7, comprises a pressure pump 20, a high pressure container valve 22, a mid sensitivity pressure container sensor 24, a pressure container 26 and a flow valve 28. The second fluidic system, shown in dash lines on FIG. 7 comprises a vacuum pump 21, a vacuum container valve 23, a mid sensitivity vacuum container sensor 25 and a vacuum container 27. The pumps 20 and 21 may be integral parts of the control and monitoring unit 16 or may be part of the medical infrastructure (hospital, ambulance, etc.) in which the system 15 of the invention is used. The pressure in each of the expandable means 7 is controlled by the simultaneous action of an inflation valve 30 connected to the first fluidic system and a deflation valve 29 connected to the second fluidic system. This way, the fluid pressure in each of the expandable means 7 can be accurately adjusted (sensitivity of about 1 mmHg) and quickly changed (about 5 mmHg/s). For each expandable means 7, a pressure sensor 31*a* and a backup pressure sensor 31*b* are provided, which report in real time the fluid pressure inside the expandable means. Additionally, a safety relief valve 32 is provided for each expandable element 7 to be used in case of emergency, to quickly decrease the fluid pressure and deflate the expandable means 7.

The actuation of the fluidic systems and valves is done through a controller 33 connected to the processing unit 18. The control and monitoring unit 16 is designed to control and/or monitor inflation/deflation of all the expandable means 7 either in parallel or in a predetermined sequence, and to independently control the pressure in each of them. For instance, by proper timing of the inflation/deflations of the expandable means, a peristaltic wave can be simulated, as described herein below.

Optionally, the control and monitoring unit 16 may comprise further sensors and/or biosensors, such as pH sensor and immunosensors, suction systems, and/or sprinkling systems. Suction systems and sprinkling systems are connected to one or more conduits going through element 2 and having at least one aperture located in the lumen of the esophagus. This aperture(s) may be located at any place in the side wall of element 2, but preferably in front of the dead volume 14 situated between two expandable means of the middle section 4 (see FIG. 5). Suction systems may be used for sucking out or sampling out fluids circulating in the esophagus of the patient, and optionally bring the sampled fluid to sensor/biosensors situated in the control and monitoring units 16 for analysis. Sprinkling systems may be used for cleaning the device 1 from biological fluids that would have been trapped close to it (e.g. in dead volume 14), and/or accelerate the transit of fluids in the direction of the stomach during the peristaltic wave simulated by the device of the invention.

Figure 8A:
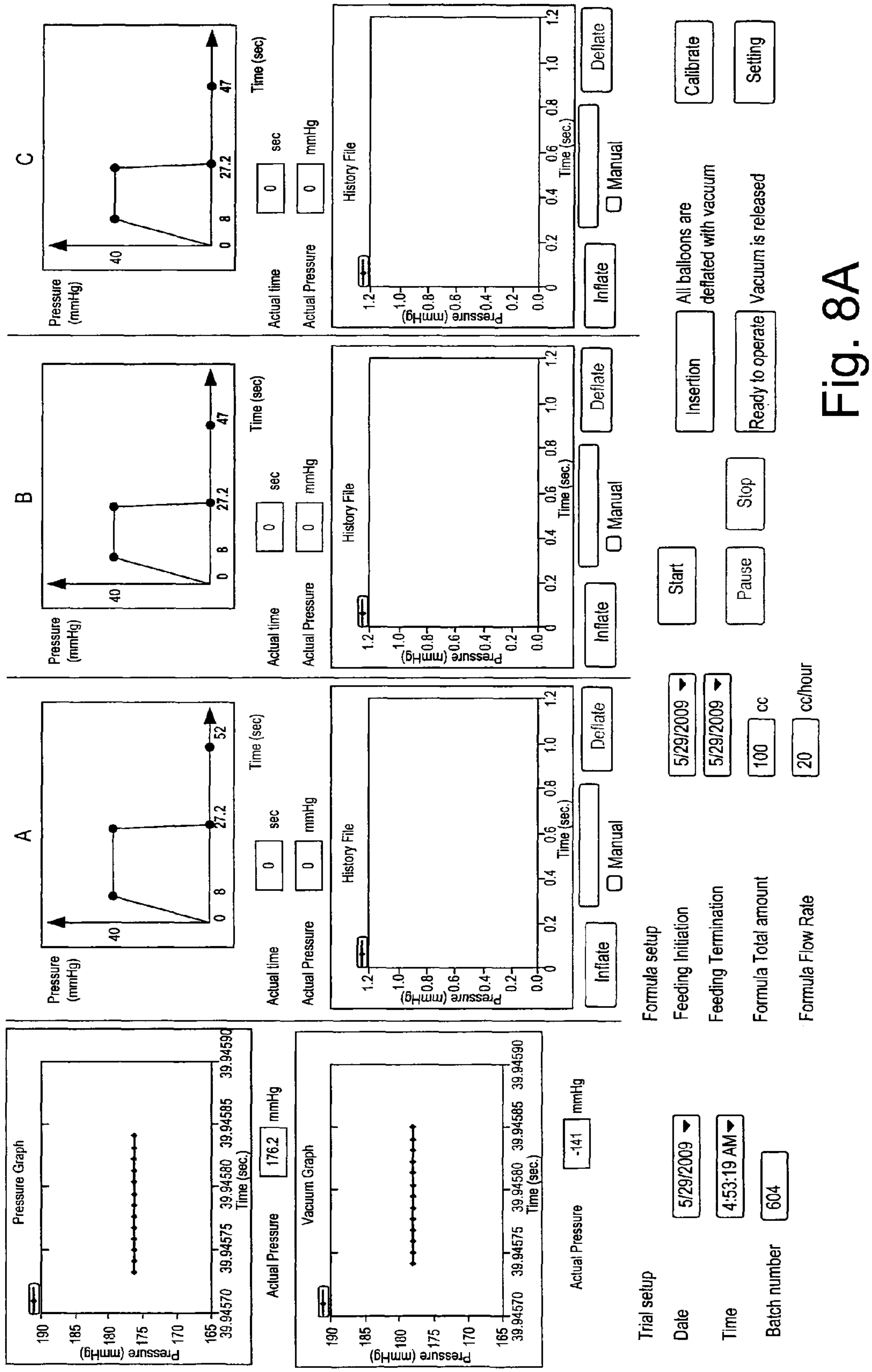
FIGS. 8A and 8B are two typical display screens from the graphical user interface of an embodiment of the software included in the system of the invention.
Figure 8B:
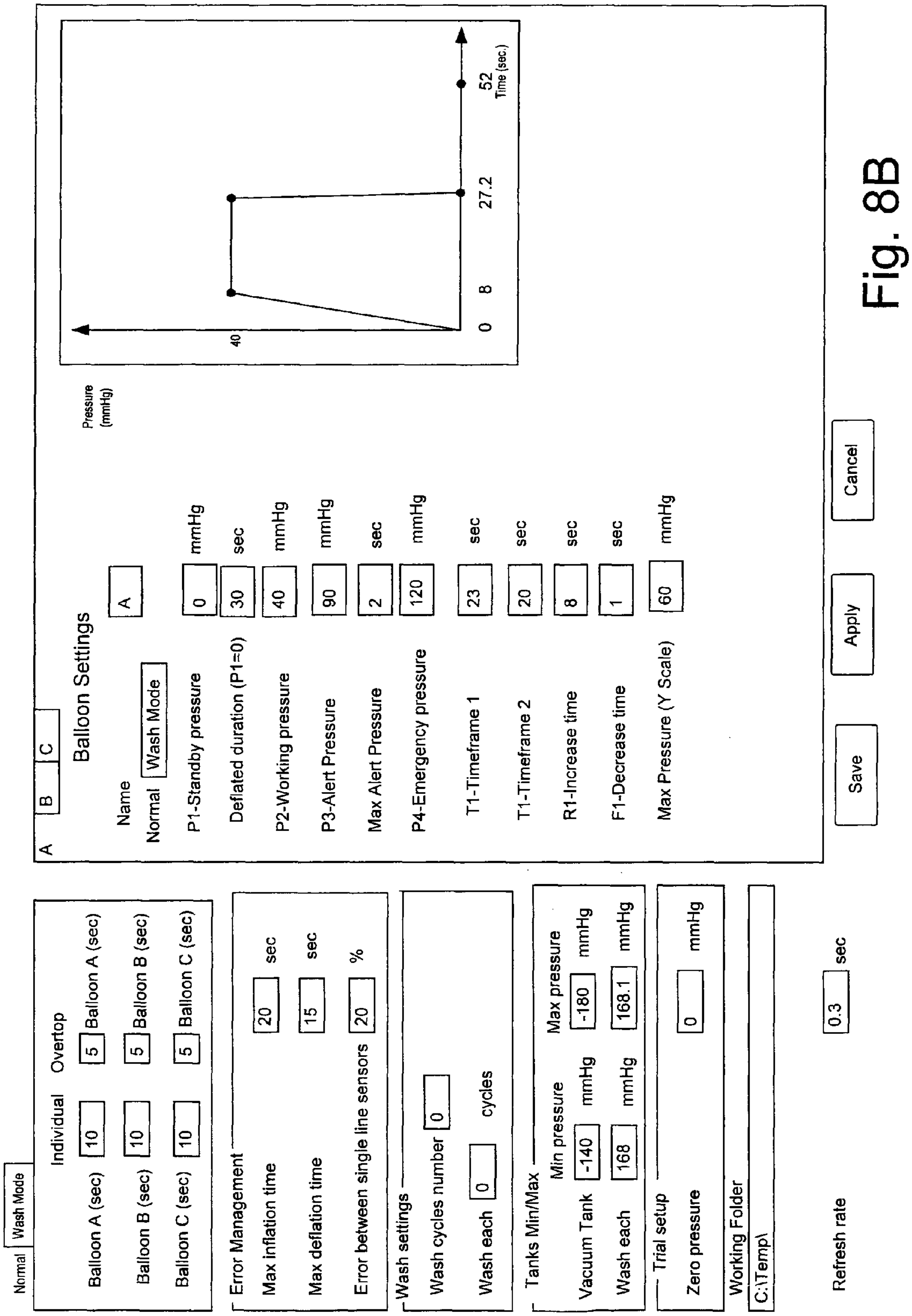

Referring now to FIGS. 8A and 8B, shown are two typical display screens from the graphical user interface of an embodiment of the software of the system of the invention. The first screen (FIG. 8A) provides the user with real-time information about the status of the different components of the system of the invention. This information is of particular importance during intubation or extubation of the enteral device, and for follow up the status of the system during standard functioning. The first screen shows, for instance:

- the actual pressure in each expandable means;
- the time elapsed since said pressure has been applied in each expandable means;
- a 2D graph showing the pressure vs. time for each expandable means;
- buttons for inflating/deflating manually the expandable means;
- total pressure provided by the first fluidic system; and
- total vacuum generated by the second fluidic system.

The second screen (FIG. 8B) enables the setting of several parameters related to the expandable means localized on the enteral feeding device and to synchronize the inflation/deflation events of the expandable means in order to simulate a peristaltic wave. The second screen (FIG. 8B) enables, for instance, the setting of the following parameters in each expandable means:

- the working pressure;
- the alert pressure;
- the emergency pressure;
- cycle timeframe;
- error management settings;
- wash settings; and
- cycle plan (T1, T2, R1, F1, Max pressure).

It is noted that the description of the control and monitoring unit and display screens shown in FIGS. 7, 8A and 8B, are provided only for purposes of illustrating the principles of the invention. Many alternate embodiments of these components of the system are contemplated by the Inventors and skilled persons can easily design embodiments that will be suitable to carry out the invention.

Figure 9:
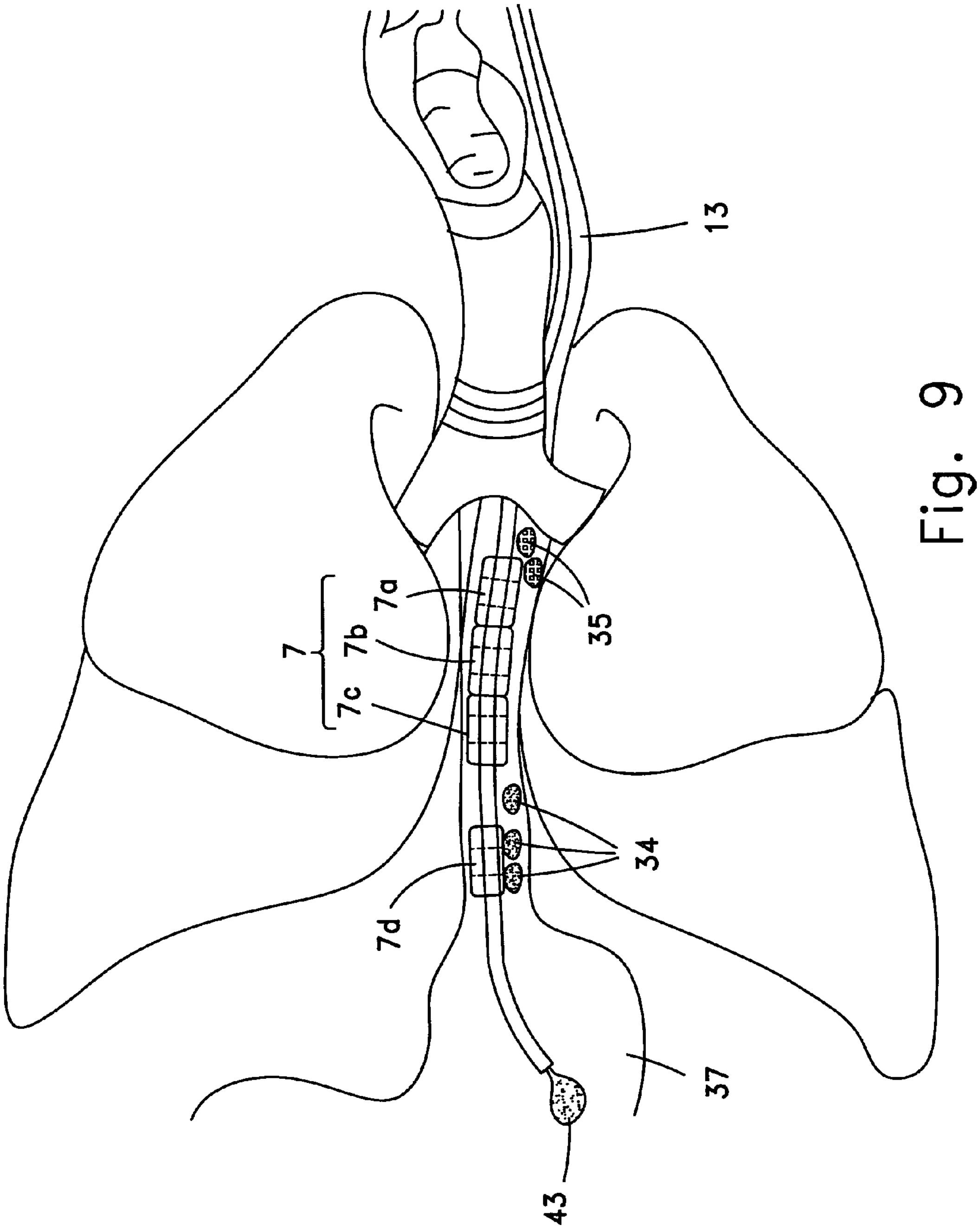
FIG. 9 is an enlarged schematic view of the distal and middle sections of a device of the invention that has been correctly positioned into the esophagus of a patient; also shown are gastrointestinal and oropharynx fluids circulating near said device.
Figure 10A:
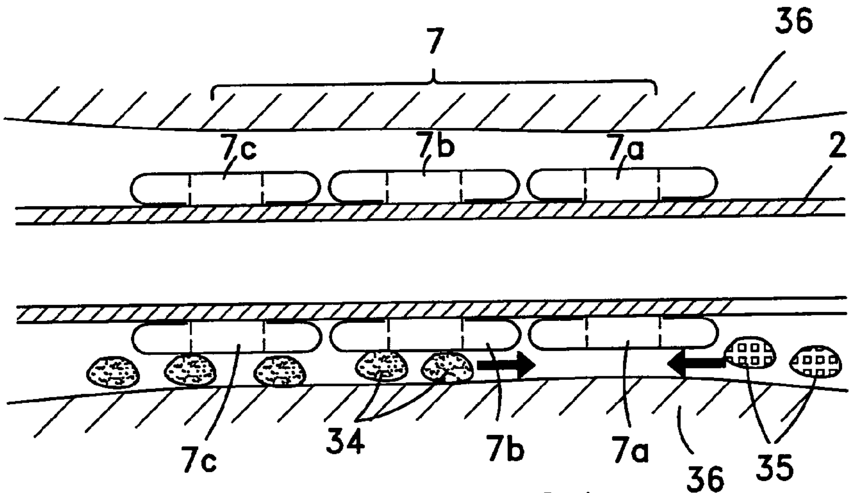
FIGS. 10A to 10F are explanatory views showing several steps of a method for feeding enterally patient, preventing gastrointestinal reflux and allowing swallowing of oropharynx fluids.
Figure 10B:
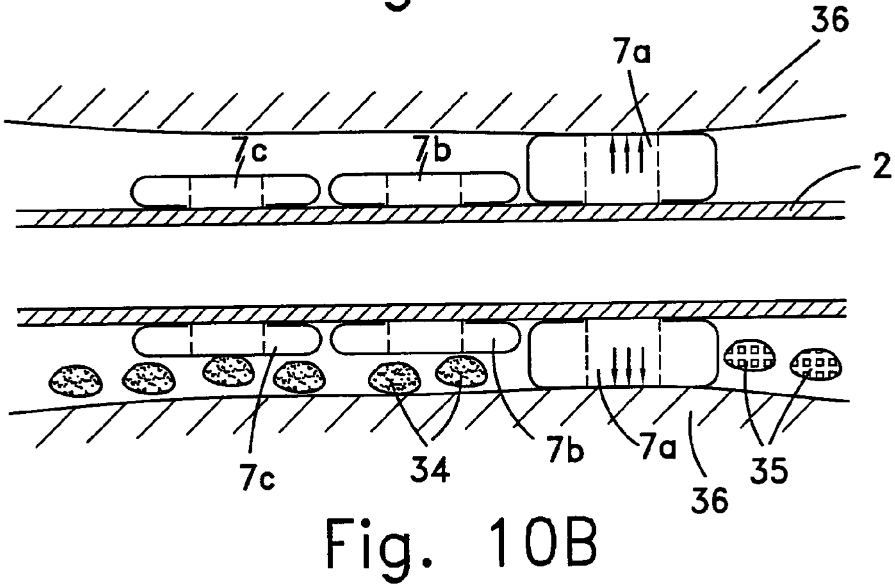
Figure 10C:
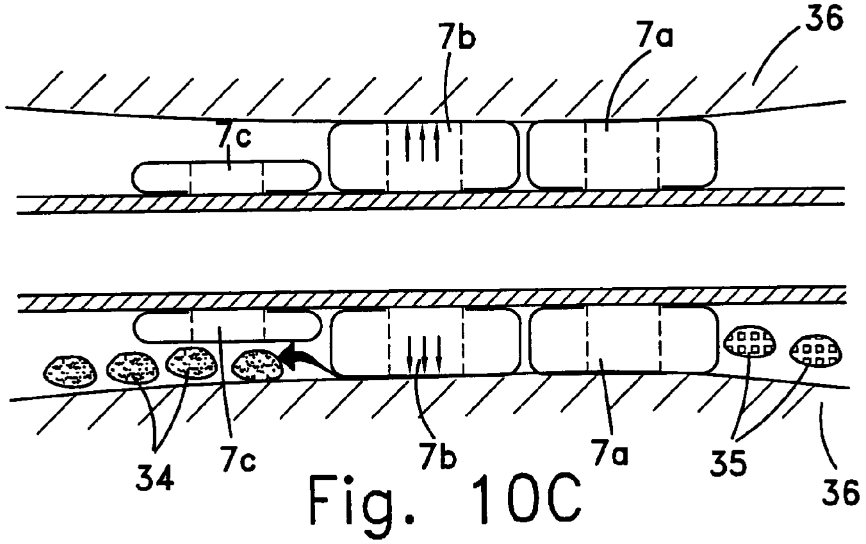
Figure 10D:
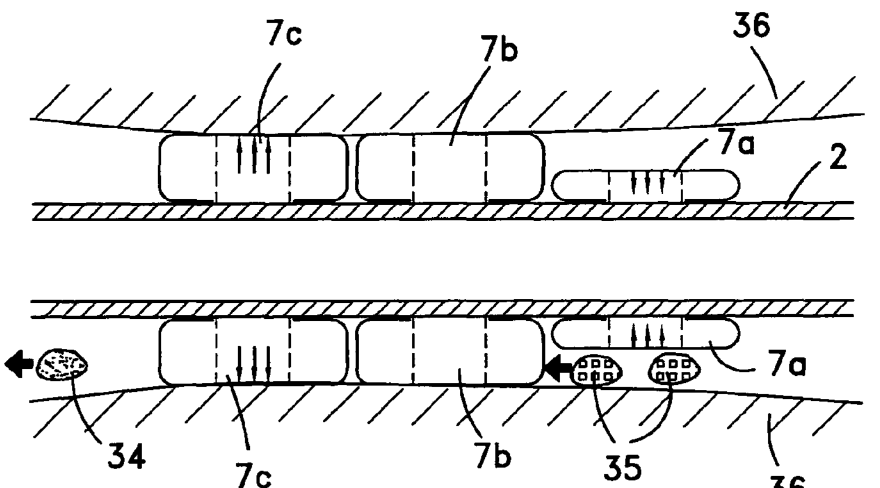
Figure 10E:
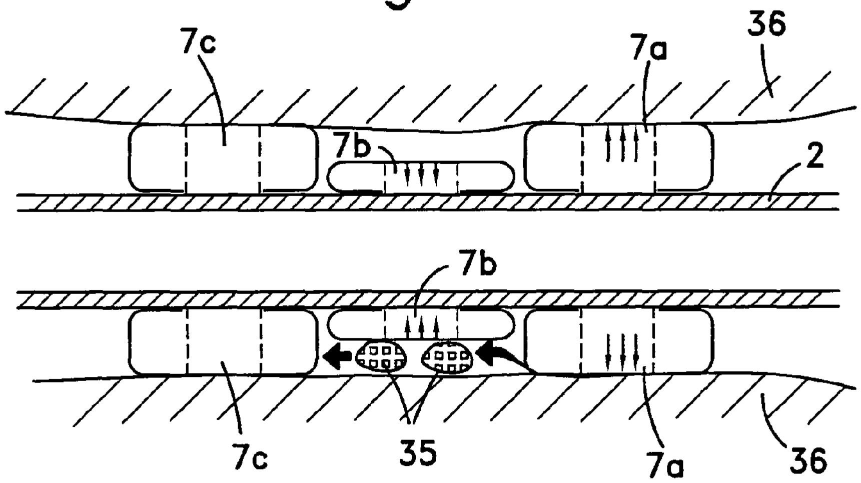
Figure 10F:
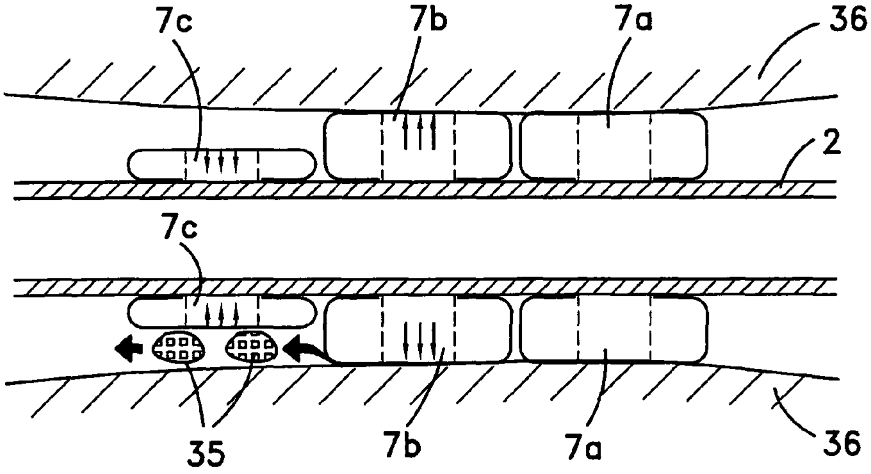

FIG. 9 shows an enlarged schematic view of the distal section 5 and the middle section 4 of a device of the invention positioned into the esophagus 13 of a patient. A nutritive solution 41 is provided into the stomach 37 through the food conveying channel 11 enclosed in the flexible element 2, and the three expandable means 7*a*, 7*b* and 7*c* are deflated. The patient is usually placed in a supine position thereby increasing the risks of gastrointestinal reflux of fluids 34 towards the oropharynx. Simultaneously, when the patient swallows, oropharynx fluids 35 move clown from the oropharynx towards the stomach. Another aspect of the invention relates to a method for pushing gastrointestinal fluids 34 back into the stomach, and allow the passage of the oropharynx fluids 35 while a patient is fed with a nutritive solution 41. The method consists in simulating two consecutive peristaltic waves using the expandable means 7 placed in the middle section 4 of the device 1 of the invention. At least three expandable means are necessary for efficiently simulating a peristaltic wave, as shown in FIGS. 10A to 10F.

In the initial stage (FIG. 10A), all the expandable means 7 are deflated and lay down on the external wall of the elongated element 2 external wall, allowing the natural transit of fluids.

In the second stage, the first expandable means 7*a* is inflated up to the maximal pressure (FIG. 10B) until the membrane of the expandable means 7*a* is in contact with the esophageal epithelium 36. This stage results in sealing the lumen and avoiding the passage of both gastrointestinal fluids 34 and oropharynx fluids 35.

In the third stage (FIG. 10C), the expandable element 7*h* is inflated up to the maximal pressure at a moderate speed (in typically 3 to 10 sec). As the space between the flexible element 2 and the esophageal epithelium 36 is reduced, the gastrointestinal fluids 34 are pushed back in direction of the stomach. The oropharynx fluids 35 remain blocked by the expandable means 7*a* which is maintained inflated.

In the fourth stage (FIG. 10D), the expandable means 7*c* is inflated up to the maximal pressure at a moderate speed (in typically 3 to 10 sec), and gastrointestinal fluids 34 are further pushed back towards the stomach. In this stage, the second peristaltic wave is also initiated by deflating the expandable means 7*a*, and the oropharynx fluids 35 are allowed to progress in direction of the stomach.

In the fifth stage (FIG. 10E), the middle expandable means 7*b* is deflated while the first expandable means 7*a* is inflated, thereby pushing the oropharynx fluids 35 downwards in the esophagus. The expandable element 7*c* is maintained inflated to block the leftovers of gastrointestinal fluids 34.

In the last stage (FIG. 10F), the expandable means 7*b* is inflated while the last expandable means 7*c* is deflated, to allow the passage of the oropharynx fluids 35.

It should be noted that the maximal pressure exerted by the expandable means onto the esophagal epithelium may be optionally calibrated by the medical staff after the correct positioning of the feeding device of the invention into a patient. This maximal pressure may vary according to the gender, age and medical antecedents of said patient and may be determined and stored in the processing unit of the system of the invention before use. Furthermore, in order to improve the efficacy of the device, the peristaltic waves simulated by the device can be synchronized with the natural esophageal peristalsis. To this end, a stimulating element can be placed in the device of the invention, and may be used to provide an electrical, chemical or mechanical signal to the muscles of the esophagus, and start "natural" peristaltic movements. The synchronization of natural and simulated peristaltic waves may lead to an optimal evacuation of the different esophageal fluids in the direction of the stomach.

As shown, the above-described method blocks the progression of the gastrointestinal fluids in the esophagus, allows the redirection of the gastrointestinal fluids towards the stomach, and enables the swallowing of the oropharynx fluids naturally secreted by the patient. This method has several advantages over the Prior Art: only low and intermittent pressures are exerted on the esophageal epithelium, which considerably reduces the risk of ischemic and venous congestion; gastrointestinal fluids are not only blocked by the expandable means but are pushed back towards the stomach by the peristaltic waves simulated by the device of the invention; oropharynx fluids can be swallowed almost naturally; the peristaltic wave generated by the system of the invention can be synchronized with the natural peristaltic movements of the esophagus. The system of the invention can be preprogrammed in a mode that simulates peristaltic at specific times, for instance in synchronization with the delivery of a nutritive solution by the feeding pump, or can be preprogrammed in a mode that achieve automatic cycles with durations and frequencies that may be variable. A combination of both modalities is also possible.

Figure 11A:
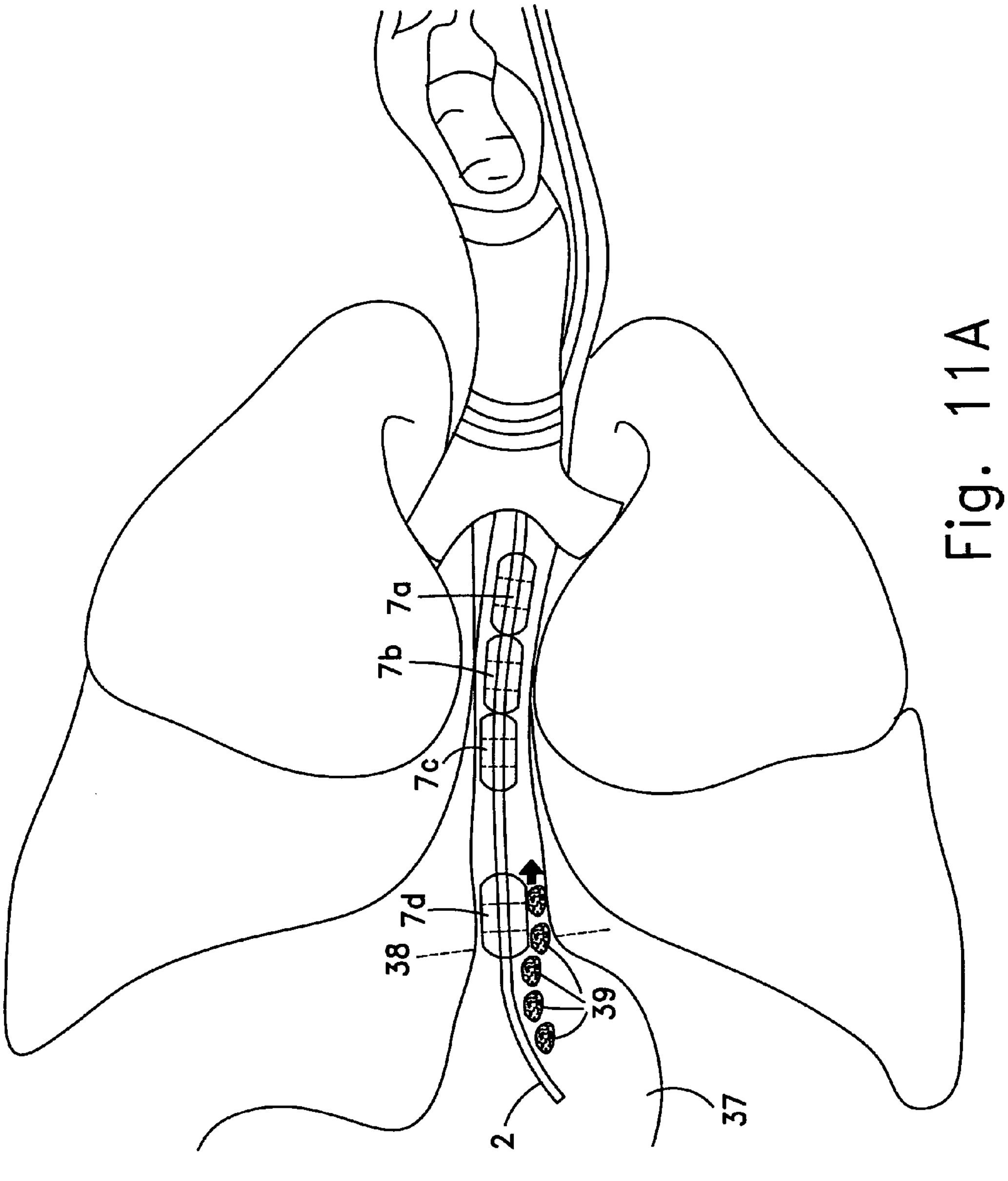
FIGS. 11A and 11B are explanatory views showing different phases of a method for preventing an enterally fed patient from vomiting.
Figure 11B:
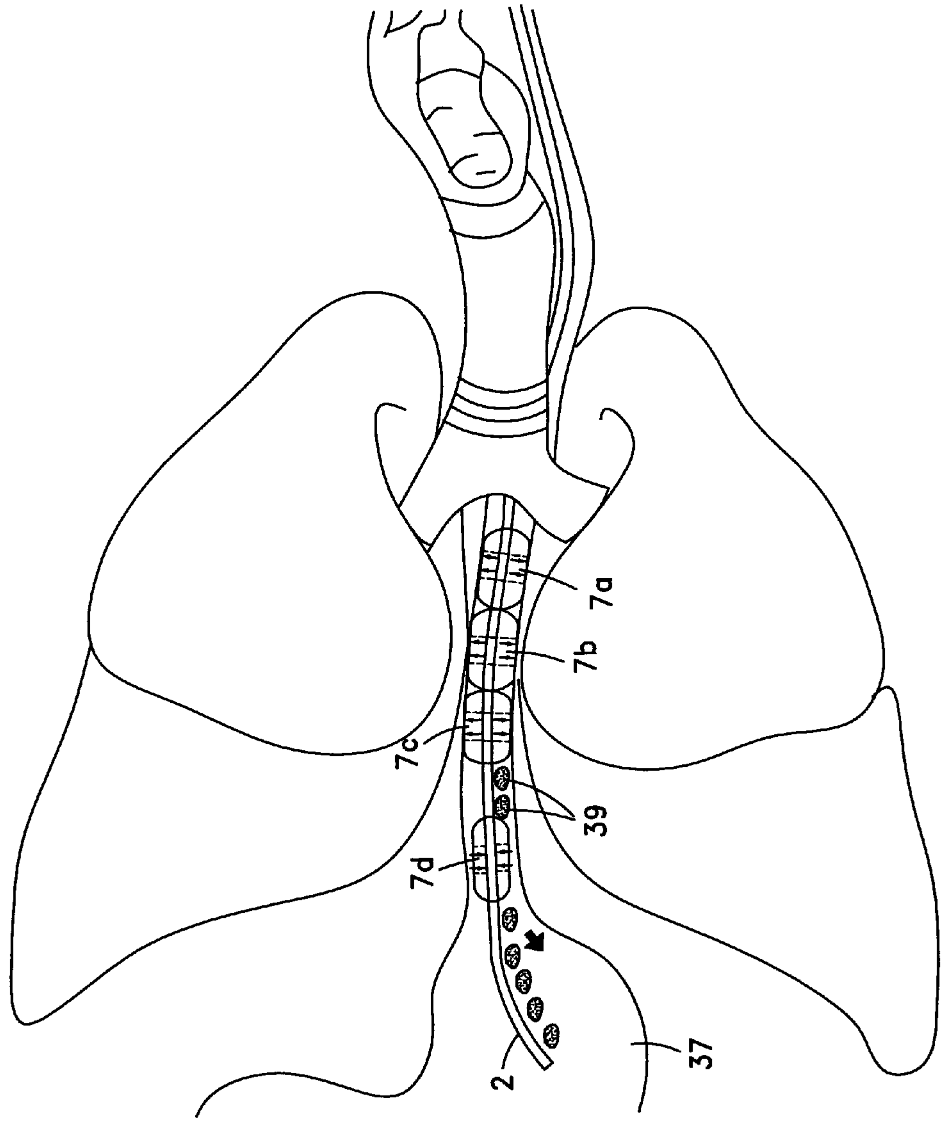

Additionally, the method of the invention enables reducing the amount of gastrointestinal fluids that reaches the oropharynx of an enterally fed patient during vomiting events. As shown in FIGS. 11A and 11B, this method preferably uses a feeding device of the invention comprising a group of expandable means 7*a*, 7*b* and 7*c* located in the middle section 4, and an additional expandable means 7*d* located in the distal section 5 of the device. After the feeding device is correctly positioned into the esophagus of the patient, with the distal end extending into the stomach 37, the expandable means 7*d* is positioned above the lower esophageal sphincter (LES) 38 and is inflated to about half of the maximal pressure (semi-inflation) and is used as a fluid sensor. As mentioned herein above, the pressure of the fluid in the body of each expandable means (internal pressure) is monitored in real-time by a pressure sensor 31 located in the control and monitoring unit 16. When an external pressure is exerted on expandable means 7*d*, it induces a significant increase of the internal pressure which is reported by the processing unit 18. Therefore, the passage of gastrointestinal fluids 34 between the semi-inflated expandable means 7*d* and the esophageal epithelium 36 can be detected and reported.

In standard conditions, expandable means 7*a*, 7*b* and 7*c* are either deflated or used to generate peristaltic waves as described herein above. When vomit 39 is expelled from the stomach 37 and reaches the expandable means 7*d*, the event is detected by the control and monitoring unit 16. The expandable means 7*d* is then totally deflated to allow the passage of fluids and the expandable means 7*a*, 7*b* and 7*c* are immediately inflated to seal the esophageal lumen. The vomit is sent back towards the stomach by gravitation, and after few seconds (typically 10 s), the initial configuration of the expandable means 7*a*, 7*b*, 7*c* and 7*d* is restored.

Figure 12A:
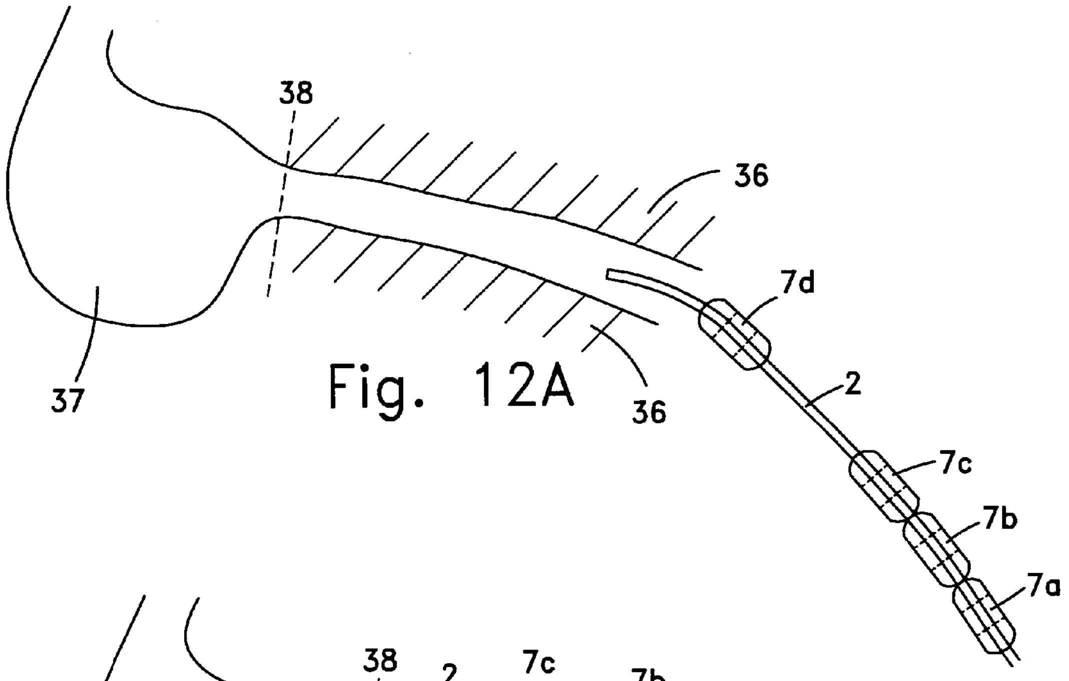
FIGS. 12A to 12E are explanatory views showing the different steps of a method used for the correct positioning of the device of the invention within the esophagus of a patient.
Figure 12B:
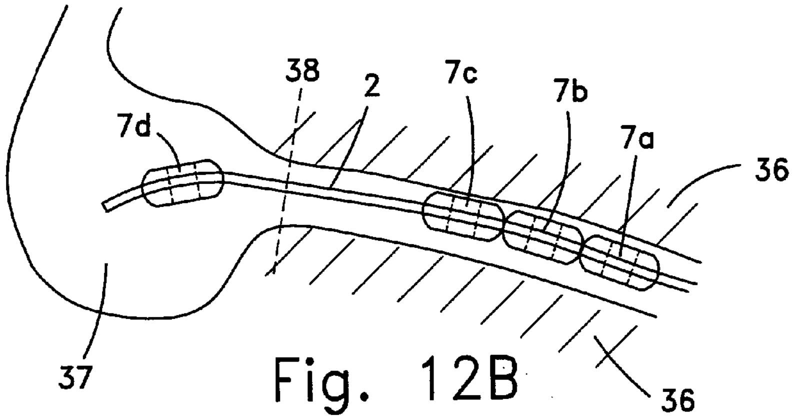
Figure 12C:
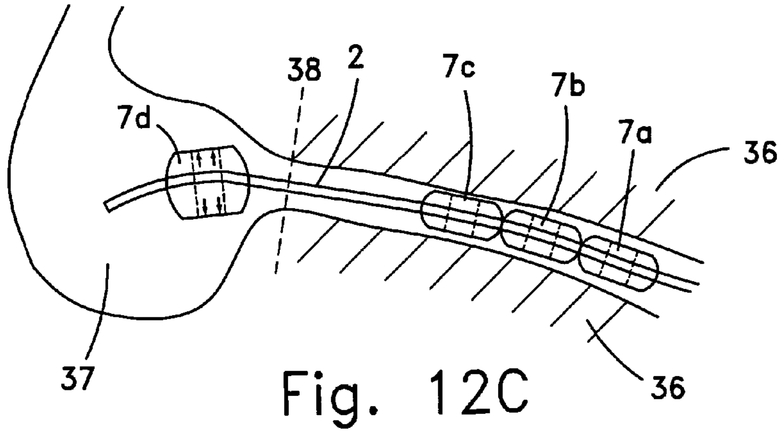
Figure 12D:
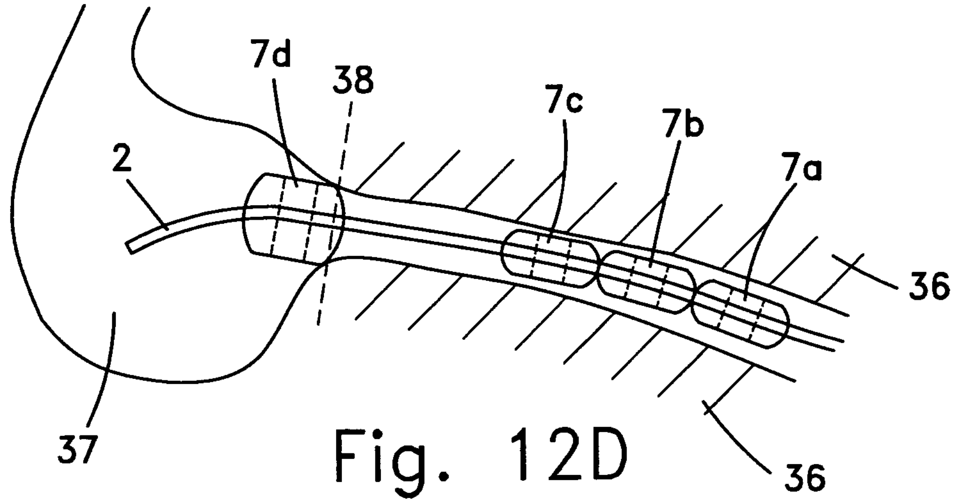
Figure 12E:
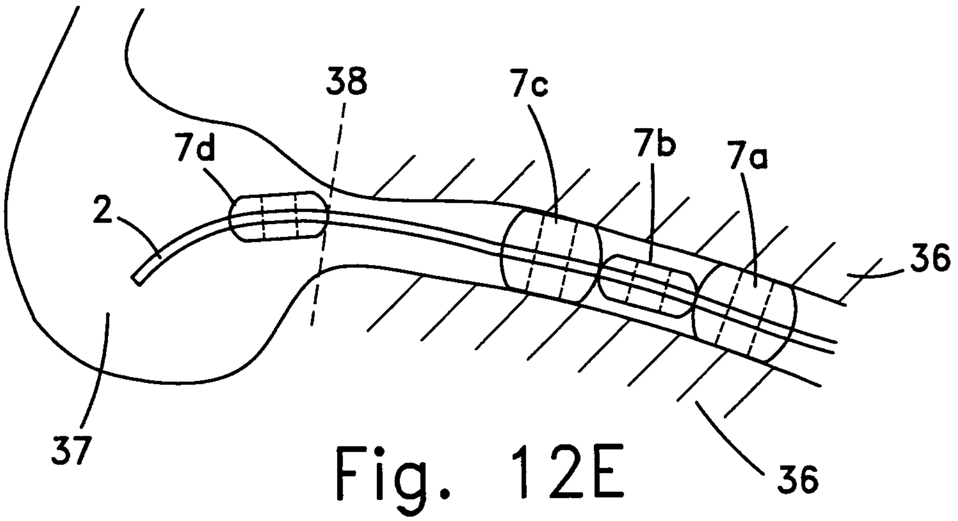

Still another aspect of the invention relates to a method for positioning the feeding device of the invention in the esophagus of a patient in need of enteral feeding. In one embodiment, correct positioning of the device of the invention is accomplished with the assistance of an external apparatus which is able to locate specific markers attached to the feeding device (such as radiopaque markers for X-ray positioning). The markers are typically embedded within the side-walls of the elongated flexible hollow element. In another embodiment, the positioning of the feeding device is performed as shown in FIGS. 12A-12E. For this embodiment, the feeding device 1 of the invention may be equipped with an expandable means 7*d* placed in the distal section 5. Prior to insertion, all the expandable means 7 equipping the feeding device are deflated (FIG. 12A). The feeding device is then inserted either via the oral route or via the nasal route into the esophagus 13 of the patient, until a positioning marker 19, placed on the proximal section 3 of the device, reaches the mouth or nose of the patient (depending from the insertion route of the device, oral or nasal). At this stage, all of the distal section 5 has been introduced into the stomach 37 of the patient. The expandable means 7*d* is then inflated at the maximal pressure and the feeding device 1 is slowly pulled back in the direction of the oropharynx until a significant increase of the pressure inside the body of the expandable means 7*d* is observed by means of a pressure sensor (not shown) connected to the expandable means 7*d*. The observed increase of pressure signifies that the expandable means 7*d* has reached the lower esophageal sphincter (LES) 38, and that the feeding device is now in a correct position. Once correctly positioned, the expandable means 7*d* is deflated and the feeding device 1 ready for use.

It is noted that the latter positioning method may be also performed without the help of the fourth expandable means 7*d* localized at the distal end. In that case, one of the expandable means 7*a*, 7*b* or 7*c*, placed in the middle section 4 of the device 1 is used as a sensor, and part of the middle section 4 is introduced into the stomach together with the distal section 5. Thereafter, one of the expandable means is inflated at the maximal pressure and the feeding device 1 is slowly pulled back in the direction of the oropharynx until a significant increase of the pressure inside the body of the chosen expandable means is observed. Then, the inflated expandable means is deflated, and the device further pulled back in the direction of the oropharynx by a predetermined distance (typically few centimeters).

Figure 13:
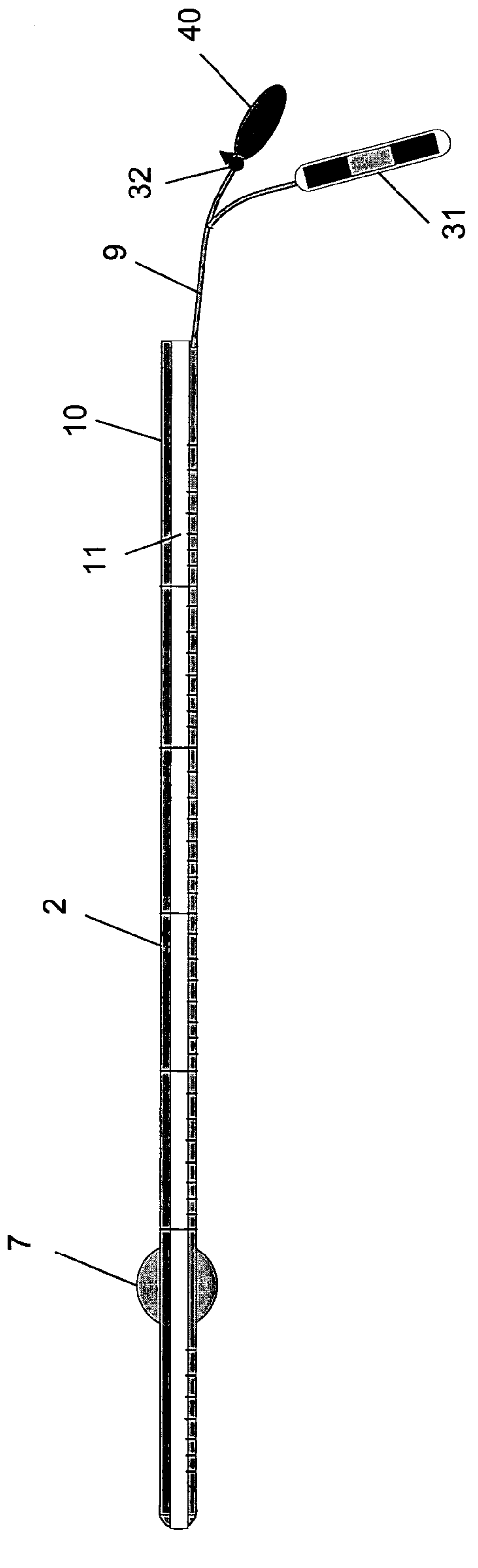
FIG. 13 is a schematic view of a feeding tube having an expandable element, a manual pump and a manometer, for easing the positioning in the esophagus of a patient.

A simplified version of the device of the invention is shown in FIG. 13 and comprises:

a) an elongated flexible hollow element 2 on which a single expandable means 7 have been placed on its distal section;
b) an inflation mechanism 40 (e.g. manual pump) connected to an fluid conveying channel 9 ending in the internal body of said expandable means;
c) a relief valve 32 connected to said fluid conveying channel,
d) a food connector 10 prolonged by a food conveying channel 11 within said hollow element 2 and ending by at least one aperture 6 in the distal end of said hollow element 2; and
e) a pressure sensor 31.

In this specific embodiment, the control and monitoring unit 16 comprises the inflation mechanism 40, a relief valve 32, and a pressure sensor 31.

Although embodiments of the invention have been described by way of illustration, it will be understood that the invention may be carried out with many variations, modifications, and adaptations, without exceeding the scope of the claims.

BIBLIOGRAPHY

1. Richards, M. J., J. R. Edwards, D. H. Culver, R. P. Gaynes, et al. 1999. Nosocomial infections in medical intensive care units in the United States, *Crit. Care Med.* 27:887-892
2. Vincent J L, Bihari D J, Suter P M, Bruining H A, White J, Nicolas-Chanoin M H, et al. The prevalence of nosocomial infection in intensive care units in Europe. Results of the European Prevalence of Infection in intensive Care (EPIC) study. EPIC International Advisory Committee. *JAMA.* 1995; 274:639-44
3. McEachern, R., and G. D. Campbell, Jr. 1998. Hospital-acquired pneumonia: epidemiology, etiology, and treatment. *Infect. Dis. Clin. N. Am.* 12:761-779
4. Papazian L, Bregeon F, Thirion X, Gregoire R, Saux P, Denis J P, et al. Effect of ventilator-associated pneumonia on mortality and morbidity. *Am J Respir Crit Care Med.* 1996; 154:91-7.
5. Baker, A. M., J. W. Meredith, and E. F. Haponik. 1996. Pneumonia in intubated trauma patients. Microbiology and outcomes. *Am. J. Respir. Crit. Care Med.* 153:343-349
6. Fagon J Y, Chastre J, Vuagnat A, Trouillet J L, Novara A, Gibert C. Nosocomial pneumonia and mortality among patients in intensive care units, *JAMA.* 1996; 275:866-9.
7. Boyce, J. M., G. Potter-Bynoe, L. Dziobek, and S. L. Solomon. 1991. Nosocomial pneumonia in Medicare patients. Hospital costs and reimbursement patterns under the prospective payment system. *Arch. Intern. Med.* 151: 1109-11.14
8. Weissman C: Nutrition in the intensive care unit. Critical Care 3:R67-R75, 1999.
9. Hadfield, R J, Sinclair, D G, Houldsworth, P E, et al Effects of enteral and parenteral nutrition on gut mucosal permeability in the critically ill. *Am J Respir Crit Care Med* 1995; 152:1545-1548
10. Marik, P E, Zaloga, G P Early enteral nutrition in acutely ill patients: a systematic review. *Crit Care Med* 2001; 29:2264-2270
11. Ibrahim, E H, Mehringer, L, Prentice, D, et al Early versus late enteral feeding of mechanically ventilated patients: results of a clinical trial. *JPEN J Parenter Enteral Nutr* 2002; 26:174-181

12. Johanson W G Jr, Pierce A K, Sanford J P, et al: Nosocomial respiratory infections with gram-negative bacilli: The significance of colonization of the respiratory tr ct. *Ann Intern Med* 1972; 77(5):701-706.

13. Bonten M J, Gaillard C A, de Leeuw P W, et al: Role of colonization of the upper intestinal tract in the pathogenesis of ventilator associated pneumonia [see comments]. *Clin. Infect. Dis.* 1997; 24(3):309-319

14. Ibanez J, Penafiel A, Raurich J M, et al: Gastroesophageal reflux in intubated patients receiving enteral nutrition: effect of supine and semirecumbent positions. *JPEN J. ParenterEnteral Nutr* 1992; 16(5):419-422

15. Torres A, Serra-Batlles J, Ros E, et al: Pulmonary aspiration of gastric contents in patients receiving mechanical ventilation: The effect of body position. *Ann Intern Med* 1992; 116(7):540-543

16. Centers for Disease Control and Prevention. Guidechannels for prevention of nosocomial pneumonia. *MMWR Morb Mortal Wkly Rep* 1997; 46(RR-1):1-79

17. Cook, D. J., S. D. Walter, R. J. Cook, L. E. Griffith, G. H. Guyatt, D. Leasa, R. Z. Jaeschke, and C. Brun-Buisson. 1998. Incidence of and risk factors for ventilator-associated pneumonia in critically ill patients. *Ann. Intern. Med.* 129:433-440

The invention claimed is:

1. A nasogastric or orogastric feeding device adapted to prevent or significantly reduce gastro-esophageal reflux from an alimentary tract to a respiratory system without damaging epithelial esophagus tissues, said nasogastric or orogastric feeding device comprising an elongated flexible hollow element having:

a) a distal section comprising at least one feeding aperture;

b) a middle section comprising at least three expandable means localized around said elongated flexible hollow element and separated by a distance of about 0 to 10 mm; and c) a proximal section comprising, a food connector, at least one fluid connector for each of said at least three expandable means, and, optionally, a positioning marker;

wherein each of said at least one fluid connector is in fluid connection with one of said expandable means via an individual fluid conveying channel, and wherein said food connector is in fluid connection with said at least one feeding aperture via a food conveying channel;

said nasogastric or orogastric feeding device being characterized in that a synchronized deflation/inflation of said at least three expendable means simulate peristaltic waves to push gastrointestinal fluids back to a stomach while allowing a passage of oropharynx fluids towards the stomach.

2. The nasogastric or orogastric feeding device of claim 1, wherein said elongated flexible hollow element is made of either a single piece of a biocompatible flexible material, or of several rigid or semi-rigid interconnected biocompatible elements.

3. The nasogastric or orogastric feeding device of claim 2, wherein said biocompatible flexible material is selected from the group consisting of silicone, latex, PVC and polyurethane.

4. The nasogastric or orogastric feeding device of claim 1, wherein said at least three expandable means have either a round or a cylindrical shape when inflated.

5. The nasogastric or orogastric feeding device of claim 1, wherein said distal section further comprises at least one expandable means.

6. The nasogastric or orogastric feeding device of claim 1, wherein radiopaque markers are embedded into a wall of said elongated flexible hollow element.

7. The nasogastric or orogastric feeding device of claim 1, further comprising at least one element selected from the group consisting of a sensing element, a stimulating element, a suction element, and a sprinkling element.

8. A system for controlling fluids motion into an esophagus of a subject, said system comprising:

a) a nasogastric or orogastric feeding device according to claim 1;

b) a control and monitoring unit;

c) a feeding unit comprising a feeding pump; and d) a processing unit comprising a processor, a memory, an input device, a display, and dedicated software, wherein said processing unit is provided either as a single element or as several separated elements.

9. The system of claim 8, wherein said control and monitoring unit comprises a first fluidic system adapted to provide a pressurized fluid, a second fluidic system adapted to provide a vacuum, a set of electrical and/or pneumatic valves, and a set of pressure sensors.

10. The system of claim 8, wherein said control and monitoring unit comprises one or more components selected from the group consisting of a sensor, a biosensor, a suction system, and a sprinkling system.

11. A method for reducing aspirations from an alimentary tract in an enterally fed patient, said method comprising the steps of:

a) providing a system as disclosed in claim 8;

b) positioning the nasogastric or orogastric feeding device provided in said system in an esophagus of said enterally fed patient;

c) feeding said enterally fed patient with a nutritive solution; and d) simulating peristaltic waves with the at least three expandable means of said nasogastric or orogastric feeding device, thereby pushing gastrointestinal fluids back to the stomach and allowing the passage of oropharynx fluids.

12. A method according to claim 11, wherein said simulated peristaltic waves are synchronized with a natural peristalsis of the esophagus.

13. A method for reducing an amount of gastrointestinal fluids that reaches an oropharynx of an enterally fed patient during vomiting events, said method comprising the steps of:

a) providing a system according to claim 8;

b) positioning the nasogastric or orogastric feeding device provided in said system in the esophagus of said enterally fed patient;

c) feeding said enterally fed patient with a nutritive solution;

d) determining, if an amount of gastrointestinal fluids is rising up into the esophagus; and e) inflating all the at least three expandable means of said nasogastric or orogastric feeding device, thereby sealing the esophagus of said enterally fed patient and redirecting gastrointestinal fluids towards the stomach.

14. A method for positioning the nasogastric or orogastric feeding device of claim 1 in an esophagus of a patient, said method comprising the steps of:

a) providing means for measuring a fluid pressure inside each of the at least three expandable means individually;

b) determining that all the at least three expandable means of said nasogastric or orogastric feeding device are deflated;

c) inserting said nasogastric or orogastric feeding device in the esophagus of said patient via either a nasal or oral route until the positioning marker reaches a mouth or nose of said patient;

d) inflating one of said at least three expandable means;

e) pulling back slowly said nasogastric or orogastric feeding device, until said means for measuring the fluid pressure indicates that the fluid pressure inside said inflated one of said at least three expandable means has risen above a predetermined threshold; and f) deflating said inflated one of said at least three expandable means; and g) optionally, further pulling back the nasogastric or orogastric feeding device by a predetermined distance.

15. A method for positioning the nasogastric or orogastric feeding device of claim 6 in the esophagus of a patient, said method comprising the steps of:

a) determining that all the at least three expandable means of said nasogastric or orogastric feeding device are deflated;

b) providing a X-ray imaging system;

c) inserting said nasogastric or orogastric feeding device in the esophagus of said patient via either a nasal or oral route;

d) using said X-ray imaging system to monitor a position of the radiopaque markers of the nasogastric or orogastric feeding device of claim 6 in the esophagus of said patient; and e) moving said nasogastric or orogastric feeding device in the esophagus of said patient until said radiopaque markers indicates that a proximal expandable means of the at least three expandable means of the middle section is placed about 5 cm beneath a carina of the patient.

* * * * *